United States Patent [19]

Caravatti et al.

[11] Patent Number: 5,093,330
[45] Date of Patent: Mar. 3, 1992

[54] STAUROSPORINE DERIVATIVES SUBSTITUTED AT METHYLAMINO NITROGEN

[75] Inventors: Giorgio Caravatti, Allschwil; Andreas Fredenhagen, Basel, both of Switzerland

[73] Assignee: Ciba-Geigy Corporation, Ardsley, N.Y.

[21] Appl. No.: 673,857

[22] Filed: Mar. 21, 1991

Related U.S. Application Data

[63] Continuation of Ser. No. 384,191, Jul. 21, 1989, abandoned, which is a continuation-in-part of Ser. No. 202,855, Jun. 6, 1988, abandoned.

[30] Foreign Application Priority Data

Jun. 15, 1987 [CH] Switzerland ............... 2244/87
Apr. 19, 1988 [CH] Switzerland ............... 1440/88
Dec. 6, 1988 [CH] Switzerland ............... 04511/88

[51] Int. Cl.$^5$ .................. A61K 31/55; C07D 498/22
[52] U.S. Cl. ............................. 514/211; 540/545
[58] Field of Search ................... 540/545; 514/211

[56] References Cited

U.S. PATENT DOCUMENTS 4,107,297  8/1978  Omara ........................ 424/122
4,735,939  4/1988  McCoy et al. ............... 514/211

FOREIGN PATENT DOCUMENTS 884238  12/1988  South Africa .

OTHER PUBLICATIONS

Tamaoki et al., Biochem. Biophys. Res. Comm., vol. 135, pp. 397–402 (1986).
Takahashi et al, J. Antibiotics, vol. 40, No. 12, pp. 1782–1784 (1987).
PCT 89/07105 Abstract.
Weinreb, Heterocycles, vol. 21, pp. 309–324 (1984).
Furusaki, J. Chem. Soc. Chem. Commun., vol. 18, 800–1 (1978).
Furusaki, Bull. Chem. Soc. Jpn., vol. 55, pp. 3681–3685 (1982).

Primary Examiner—Mark L. Berch
Attorney, Agent, or Firm—JoAnn Villamizar

[57] ABSTRACT

N-substituted derivatives of staurosporine of the general formula

[Stau]—N(CH$_3$)—R    (I)

in which [Stau] represents a residue of the partial formula

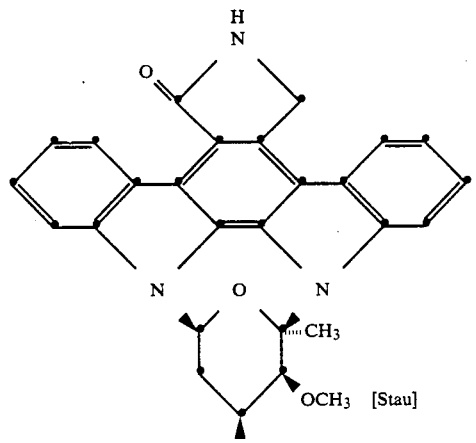

and R represents a hydrocarbyl radical R$^o$ or an acyl radical Ac, which radicals preferably have a maximum of 30 carbon atoms, and salts of compounds of the formula I having salt-forming properties, are distinguished as selective inhibitors of proteinkinase C. They are manufactured by conventional alkylation or acylation, respectively, of staurosporine.

10 Claims, No Drawings

STAUROSPORINE DERIVATIVES SUBSTITUTED AT METHYLAMINO NITROGEN

This application is a continuation of application Ser. No. 384,191, filed July 21, 1989 now abandoned.

The present invention relates to derivatives of staurosporine that are substituted at the methylamino nitrogen atom, especially those of the general formula

[Stau]—N(CH$_3$)—R    (I)

in which [Stau] represents a residue of the partial formula

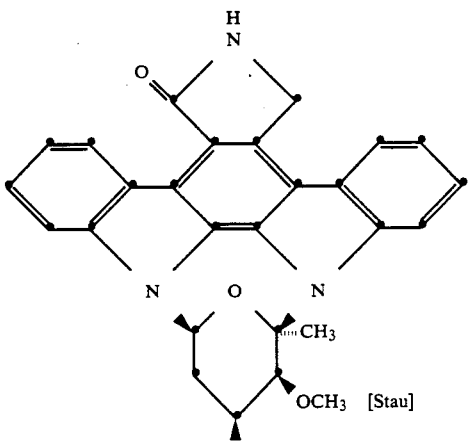

and R represents a hydrocarbyl radical R$^o$ or an acyl radical Ac, which radicals preferably have a maximum of 30 carbon atoms, and to salts of compounds of formula I having salt-forming properties.

The invention also relates to processes for the manufacture of the above-defined compounds, to pharmaceutical preparations containing those compounds and the manufacture thereof, to the medicinal use of those compounds and preparations and to the corresponding therapeutic method.

Staurosporine of the formula [Stau]—NH—CH$_3$ (II) (for the meaning of the residue [Stau] see above), the basic material of the compounds of the invention, was isolated as early as 1977 from *Streptomyces staurosporeus* cultures, and examined for antimicrobial activity, AWAYA, TAKAHASHI and ŌMURA, sp. nov. AM 2282, cf. Omura, S.; Iwai, Y.; Hirano, A.; Nakagawa, A.; Awaya, J.; Tsuchiya, H.; Takahashi, Y.; and Masuma, R.: J. Antibiot. 30, 275-281 (1977). In the course of this examination it was also discovered that the compound is active against yeast-like microorganisms and fungi (MIC of approximately 3-25 mcg/ml), having an LD$_{50}$ of 6.6 mg/kg (mice, intraperitoneal) in the form of the hydrochloride. Recently it has been demonstrated in extended screening, cf. Tamaoki, T.; Nomoto, H.; Takahashi, I.; Kato, Y.; Morimoto, M.; and Tomita, F.: Biochem. and Biophys. Research Commun. 135 (No. 2), 397-402 (1986), that the compound has a strong inhibiting action against proteinkinase C (from rats' brains).

Phospholipid- and calcium-dependent proteinkinase C exists within the cell in several forms and takes part in various fundamental processes, such as signal transmission, proliferation and differentiation, as well as, also, the diffusion of hormones and neurotransmitters. As is known, this enzyme is activated either by hydrolysis of phospholipids of the cell membrane brought about by way of receptors, or by direct interaction with certain tumour-promoting active substances. The sensitivity of the cell to the signal transmission brought about by the receptor can be influenced substantially by modification of the activity of protein-kinase C (as signal transmitter). Compounds that are capable of selective modification of the activity of proteinkinase C may be used as tumour-inhibiting, inflammation-inhibiting, immunomodulating and antibacterial active substances and, moreover, are of interest as preparations for combating arteriosclerosis and diseases of the cardiovascular system and central nervous system.

Although staurosporine has a strong inhibiting action on proteinkinase C (see above), it also strongly inhibits other proteinkinases and therefore does not have the selectivity that would be necessary for a therapeutic use. Surprisingly, it has now been demonstrated that when the hydrogen atom is removed from the methylamino group of staurosporine by substitution, the resulting N-substituted derivatives selectively retain the inhibiting activity of staurosporine against proteinkinase C, but are substantially less active against other proteinkinases. With this significant increase in selectivity, the compounds of the invention now also meet the important requirement for therapeutic use in the above-mentioned ranges of indication, especially for influencing cell proliferation.

For determination of the inhibiting action on proteinkinase C first proteinkinase C was extracted from porcine brain and then purified according to the method described by T. Uchida and C. R. Filburn in J. Biol. Chem. 259, 12311-12314 (1984). To determine the inhibiting action of the proteinkinase the method of D. Fabro et al. according to Arch. Biochem. Biophys. 239, 102-111 (1985) was applied. A significant inhibition of proteinkinase C resulted at a concentration of about 0.01 μM/l.

Accordingly, the compounds of formula I and their pharmaceutically acceptable salts can be employed, for example, as medicaments especially for tumour-inhibiting, inflammation-inhibiting, immunomodulating, and antibacterial use, and also as preparations for combating arteriosclerosis, diseases of the cardiovascular system and of the central nervous system. The present invention also relates to the use of the compounds of the invention for the manufacture of medicaments, for example for the above-described use, for the therapeutic and prophylactic treatment of the human body, and also the animal body. The industrial manufacture of the active ingredients may also be included.

The hydrocarbyl radical (hydrocarbon radical) Ro is an acyclic (aliphatic), carbocyclic or carbocyclic-acyclic hydrocarbon radical having a maximum total number of carbon atoms of preferably 30 and, especially, 18, which may be saturated or unsaturated, unsubstituted or substituted. It may also contain instead of one, two or more carbon atoms the same or different hetero atoms, such as, especially, oxygen, sulphur and nitrogen, in the acyclic and/or cyclic moiety; in the latter case it is referred to as a heterocyclic radical (heterocyclyl radical) or a heterocyclic-acyclic radical.

Unsaturated radicals are those that contain one or more, especially conjugated and/or isolated, multiple bonds (double and/or triple bonds). The term "cyclic radicals" also includes aromatic radicals, for example those in which at least one 6-membered carbocyclic ring or one 5- to 8-membered heterocyclic ring contains the maximum number of non-cumulated double bonds. Carbocyclic radicals in which at least one ring is in the form of a 6-membered aromatic ring (that is to say a benzene ring) are referred to as aryl radicals.

Unless stated otherwise, organic radicals referred to herein as "lower" contain a maximum of 7, preferably a maximum of 4, carbon atoms.

An acyclic unsubstituted hydrocarbon radical is especially a straight or branched lower alkyl, lower alkenyl, lower alkadienyl or lower alkynyl radical. Lower alkyl is, for example, methyl, ethyl, n-propyl, isopropyl, n-butyl, isobutyl, sec.-butyl or tert.-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkynyl is, for example, propargyl or 2-butynyl. In corresponding unsaturated radicals, the double bond is located especially in a position higher than the $\alpha$-position to the free valency.

A carbocyclic hydrocarbon radical is especially a mono-, bi- or polycyclic cycloalkyl, cycloalkenyl or cycloalkadienyl radical, or a corresponding aryl radical. Preferred are radicals having a maximum of 14, especially 12, ring carbon atoms and having 3- to 8-membered, preferably 5- to 7-membered, especially 6-membered, rings; they may also carry one or more, for example two, acyclic radicals, for example those mentioned above, and especially lower alkyl radicals, or other carbocyclic radicals. Carbocyclic-acyclic radicals are those in which an acyclic radical, especially one having a maximum of 7, preferably a maximum of 4, carbon atoms, such as, especially, methyl, ethyl or vinyl, carries one or more of the carbocyclic, optionally aromatic radicals defined above. Mention is made especially of cycloalkyl-lower alkyl and aryl-lower alkyl radicals, and also analogues thereof unsaturated in the ring and/or chain, that carry the ring at the terminal carbon atom of the chain.

Cycloalkyl has especially from 3 up to and including 10 carbon atoms and is, for example, cyclopropyl, cyclobutyl, cyclopentyl, cyclohexyl, cycloheptyl and cyclooctyl, as well as bicyclo[2,2,2]octyl, 2-bicyclo[2,2,1-]heptyl and adamantyl, which may also be substituted by 1, 2 or more, for example lower, alkyl radicals, especially methyl radicals; cycloalkenyl is, for example, one of the monocyclic cycloalkyl radicals already mentioned that carry a double bond in the 1-, 2- or 3-position. Cycloalkyl-lower alkyl or -lower alkenyl is, for example, a cycloalkyl-methyl, -1-or -2-ethyl, 1- or -2-vinyl, -1-, -2- or -3-propyl or -1, -2- or -3-allyl radical substituted by one of the above-mentioned cycloalkyl radicals, those substituted at the end of the linear chain being preferred.

An aryl radical is especially a phenyl radical, or also a naphthyl radical, such as a 1- or 2-naphthyl radical, a biphenylyl radical, such as, especially, 4-biphenylyl, or also an anthryl, fluorenyl or azulenyl radical, and the aromatic analogues thereof having one or more saturated rings. Preferred aryl-lower alkyl and -lower alkenyl radicals are, for example, phenyl-lower alkyl or phenyl-lower alkenyl having a terminal phenyl radical, such as, for example, benzyl, phenethyl, 1-, 2- or 3-phenylpropyl, diphenylmethyl (benzhydryl), trityl and cinnamyl, and also 1- or 2-naphthylmethyl. Of the aryl radicals that carry acyclic radicals, such as lower alkyl, mention is made especially of o-, m-and p-tolyl and xylyl radicals with variously positioned methyl radicals.

Heterocyclic radicals, including heterocyclic-acyclic radicals, are especially monocyclic, but also bi- or polycyclic, aza-, thia-, oxa-, thiaza-, oxaza-, diaza-, triaza- or tetraza-cyclic radicals of aromatic character, and also corresponding partially saturated or, especially, fully saturated, heterocyclic radicals of that kind, it being possible, optionally, for such radicals, for example like the above-mentioned carbocyclic or aryl radicals, to carry further acyclic, carbocyclic or heterocyclic radicals and/or to be mono-, di- or poly-substituted by functional groups. The acyclic moiety in heterocyclic-acyclic radicals has, for example, the meaning given for the corresponding carbocyclicacyclic radicals. If a heterocyclyl radical as a direct substituent $R^o$ is positioned at the methylamino group of the staurosporine, then its free valency must originate from one of its carbon atoms. It is especially an unsubstituted or substituted monocyclic radical containing a nitrogen, oxygen or sulphur atom, such as 2-aziridinyl, and especially an aromatic radical of that kind, such as pyrryl, for example 2-pyrryl or 3-pyrryl, pyridyl, for example 2-, 3- or 4-pyridyl, and also thienyl, for example 2- or 3-thienyl, or furyl, for example 2-furyl; analogous bicyclic radicals having a nitrogen, oxygen or sulphur atom are, for example, indolyl, such as 2- or 3-indolyl, quinolyl, such as 2- or 4-quinolyl, isoquinolyl, such as 3- or 5-isoquinolyl, benzofuranyl, such as 2-benzofuranyl, chromenyl, such as 3-chromenyl, or benzothienyl, such as 2- or 3-benzothienyl; preferred monocyclic and bicyclic radicals having several hetero atoms are, for example, imidazolyl, such as 2-imidazolyl, pyrimidinyl, such as 2- or 4-pyrimidinyl, oxazolyl, such as 2-oxazolyl, isoxazolyl, such as 3-isoxazolyl, or thiazolyl, such as 2-thiazolyl, or benzimidazolyl, such as 2-benzimidazolyl, benzoxazolyl, such as 2-benzoxazolyl, or quinazolyl, such as 2-quinazolinyl. Also suitable are corresponding partially or, especially, fully saturated analogous radicals, such as 2-tetrahydrofuryl, 2- or 3-pyrrolidyl, 2-, 3- or 4-piperidyl, and also 2- or 3-morpholinyl, 2-or 3-thiomorpholinyl, 2-piperazinyl and N,N'-bis-lower alkyl-2-piperazinyl radicals. These radicals may also carry one or more acyclic, carbocyclic or heterocyclic radicals, especially those mentioned above. Heterocyclic-acyclic radicals are derived especially from acyclic radicals having a maximum of 7, preferably a maximum of 4, carbon atoms, for example those mentioned above, and may carry one, two or more heterocyclic radicals, for example those mentioned above, it also being possible for the ring to be bonded to the chain by one of its nitrogen atoms.

As has already been mentioned, a hydrocarbyl radical (including a heterocyclyl radical) may be substituted by one, two or more identical or different substitutents (functional groups); the following substituents are especially suitable: free, etherified and esterified hydroxy groups; mercapto and also lower alkylthio groups and optionally substituted phenylthio groups; halogen atoms, such as chlorine and fluorine, but also bromine and iodine; oxo groups present in the form of formyl (that is aldehydo) and keto groups, and also in the form of corresponding acetals and ketals, respectively; azido and nitro groups; primary, secondary and, preferably, tertiary amino groups, or conventionally protected primary or secondary amino groups, acylamino groups and diacylamino groups, and also optionally functionally modified sulpho groups, such as sulphamoyl groups, or sulpho groups in salt form. None of these functional groups may be positioned at the carbon atom from which the free valency originates and preferably they are separated from that carbon atom by two or even several carbon atoms. The hydrocarbyl radical may also carry free and functionally modified carboxy groups, such as carboxy groups in salt form or esterified carboxy groups, carbamoyl, ureido or guanidino groups each optionally carrying one or two hydrocarbon radicals, and cyano groups.

An etherified hydroxy group present as a substituent in the hydrocarbyl radical is, for example, a lower alkoxy group, such as a methoxy, ethoxy, propoxy, isopropoxy, butoxy or tert.-butoxy group, which may also be substituted. Such a lower alkoxy group may be substituted, for example mono-, di- or poly-substituted, by halogen atoms, especially in the 2-position, such as in 2,2,2-trichloroethoxy, 2-chloroethoxy or 2-iodoethoxy, or may be substituted, in each case preferably monosubstituted, especially in the 2-position, by hydroxy or lower alkoxy radicals, such as in 2-methoxyethoxy. An especially preferred form of the etherified hydroxy groups consists in oxaalkyl radicals in which, in a preferably linear alkyl radical, one or more carbon atoms have been replaced by oxygen atoms that are separated from one another preferably by several (especially 2) carbon atoms, so that they form a group —(—O—CH$_2$CH$_2$—)n— that is optionally repeated several times in which n=from 1 to 14. Such etherified hydroxy groups are also optionally substituted phenoxy radicals and phenyl-lower alkoxy radicals, such as, especially, benzyloxy, benzhydryloxy and triphenylmethoxy (trityloxy), and also heterocyclyloxy radicals, such as, especially, 2-tetrahydropyranyloxy. The groupings methylenedioxy and ethylenedioxy are to be regarded as special etherified hydroxy groups, the former as a rule bridging 2 adjacent carbon atoms, especially in aryl radicals, and the latter being bonded at one and the same carbon atom and being regarded as a protecting group for oxo. There are to be understood by etherified hydroxy groups in this context also silylated hydroxy groups, such as those present, for example, in tri-lower alkylsilyloxy, such as trimethylsilyloxy and dimethyl-tert.-butylsilyloxy, or in phenyl-di-lower alkylsilyloxy or lower alkyl-diphenylsilyloxy.

An esterified hydroxy group present as a substituent in the hydrocarbyl radical carries an acyl radical Ac as defined hereinafter, especially one having a maximum of 12 carbon atoms, or is lactonised by a carboxy group also present in the hydrocarbyl radical.

An esterified carboxy group present as a substituent in the hydrocarbyl radical is one in which the hydrogen atom has been replaced by one of the above-characterised hydrocarbon radicals, preferably a lower alkyl or phenyl-lower alkyl radical; there may be mentioned as an example of an esterified carboxy group lower alkoxycarbonyl, or phenyl-lower alkoxycarbonyl optionally substituted in the phenyl moiety, especially the methoxy-, ethoxy-, tert.-butoxy- or benzyloxy-carbonyl group, and also a lactonised carboxy group.

A primary amino group —NH$_2$ as substituent of the hydrocarbyl radical may also be present in protected form as a corresponding acylamino group of the formula —NH—Ac$^o$, in which Ac$^o$ has the meaning given hereinafter. A secondary amino group carries instead of one of the two hydrogen atoms a hydrocarbyl radical, preferably an unsubstituted hydrocarbyl radical, such as one of those mentioned above, especially lower alkyl, and may also be present in a protected form as an acylamino group derived therefrom containing a monovalent acyl radical Ac$^o$ defined hereinafter.

The acyl radical Ac$^o$ acting as amino-protecting group is derived preferably from a carbonic acid semiderivative and is preferably a lower alkoxycarbonyl or aryl-lower alkoxycarbonyl radical optionally substituted especially by lower alkyl, lower alkoxy, nitro and/or by halogen, such as methoxycarbonyl, ethoxycarbonyl, tert.-butoxycarbonyl, 2,2,2-trichloroethoxycarbonyl, 2-iodoethoxycarbonyl, benzyloxycarbonyl, 2-phenyl-2-propoxycarbonyl, 2-p-tolyl-2-propoxycarbonyl, 2-(p-biphenylyl)-2-propoxycarbonyl or 9-fluorenylmethoxycarbonyl.

A tertiary amino group present as a substituent in the hydrocarbyl radical carries 2 different or, preferably, identical hydrocarbyl radicals (including the heterocyclic radicals), such as the above-characterised unsubstituted hydrocarbyl radicals, especially lower alkyl.

A preferred amino group is one of the formula

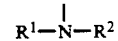

in which each of R$^1$ and R$^2$, independently of the other, represents hydrogen, unsubstituted acyclic C$_1$-C$_7$-hydrocarbyl (such as, especially, a C$_1$-C$_4$-alkyl or C$_1$-C$_4$-alkenyl) or monocyclic aryl, aralkyl or aralkenyl having a maximum of 10 carbon atoms each optionally substituted by C$_1$-C$_4$-alkyl, C$_1$-C$_4$-alkoxy, halogen and/or by nitro, it being possible for the carbon-containing radicals to be bonded to one another by a carbon-carbon bond or by an oxygen or sulphur atom or an optionally hydrocarbyl-substituted nitrogen atom. In such a case they form, together with the nitrogen atom of the amino group, a nitrogen-containing heterocyclic ring. The following may be mentioned as examples of especially preferred free amino groups: di-lower alkylamino, such as dimethylamino, diethylamino, pyrrolidino, piperidino, morpholino, thiomorpholino and piperazino or 4-methylpiperazino, and diphenylamino and dibenzylamino each optionally substituted, especially in the phenyl moiety, for example by lower alkyl, lower alkoxy, halogen and/or by nitro; and the following may be mentioned as examples of especially preferred protected amino groups: lower alkoxycarbonylamino, such as tert.-butoxycarbonylamino, phenyl-lower alkoxycarbonylamino, such as 4-methoxybenzyloxycarbonylamino, and also 9-fluorenylmethoxycarbonylamino.

Unless specified to the contrary, hereinbefore and hereinafter aromatic carbocyclic and heterocyclic hydrocarbyl radicals may be mono- or polysubstituted, such as di- or tri-substituted, especially by C$_1$-C$_4$-alkyl, C$_1$-C$_4$-alkoxy, halogen, nitro, trifluoromethyl, also carboxy, C$_1$-C$_4$-alkoxycarbonyl, methylenedioxy, and/or by cyano. Reduced details hereinbefore and hereinafter concerning substituents are to be regarded as preferences.

Preferred compounds of formula I according to the invention are, for example, those in which R represents a hydrocarbyl radical R$^o$ with the following preferred meanings of an acyclic hydrocarbyl radical: a C$_1$-C$_{20}$-alkyl radical, a C$_2$-C$_{20}$ hydroxyalkyl radical of which the hydroxy group is in any position other than the 1-position and is preferably in the 2-position, a cyano-[C$_1$-C$_{20}$]-alkyl radical of which the cyano group is preferably in the 1- or ω-position, or a carboxy-[$C_1$-$C_{20}$]-alkyl radical of which the carboxy group is preferably in the 1- or ω-position and may optionally also be present in salt form or in the form of a $C_1$-$C_4$-alkyl ester ($C_1$-$C_4$-alkoxycarbonyl) or benzyl ester (benzyloxycarbonyl) group, as well as a $C_3$-$C_{20}$-alkenyl radical of which the free valency is not at the same carbon atom as the double bond, all of the mentioned radicals, apart from those with a $C_3$-$C_5$-alkyl basic structure, having a linear (unbranched) alkyl chain; further, also a linear (mono-, di- to hexa)oxaalkyl radical having from 4 to 20 chain members in which one or more of the carbon atoms, from C-3 on, of a linear $C_4$-$C_{20}$-alkyl radical has/have been replaced by oxygen atoms that are separated from each other by at least 2 carbon atoms and are preferably in positions 3, 6, 9, 12, 15 and 18.

Preferred compounds of formula I according to the invention are also those in which R represents a hydrocarbyl radical $R^o$ with the following preferred meanings of a carbocyclic or heterocyclic, and also carbocyclic-acyclic or heterocyclic-acyclic, hydrocarbyl radical: a bicyclic or preferably monocyclic aryl radical, especially phenyl, and also naphthyl, which may carry one or more of the following substituents: halogen atoms, especially fluorine, chlorine and bromine, $C_1$-$C_4$-alkyl radicals, especially methyl, $C_1$-$C_4$-alkoxy groups, especially methoxy, methylenedioxy, nitro groups and/or carboxy groups, which may be free, in salt form or in the form of $C_1$-$C_4$-alkyl esters, especially methoxycarbonyl or ethoxycarbonyl. Preferably, the aryl radicals carry no more than 2 substituents, especially substituents of the same kind, or carry only one substituent; more especially, they are unsubstituted. A preferred heterocyclic hydrocarbyl radical (heterocyclyl radical) is, for example, one that is analogous to those aryl radicals given special mention hereinbefore and that contains instead of one or 2 carbon atoms in each case a hetero atom, especially nitrogen, such as a pyridyl or quinolyl radical, or a quinazolyl radical, the free valency being located at a carbon atom and also accordingly being substitutable. Preferred carbocyclic-acyclic and heterocyclic-acyclic hydrocarbyl radicals are those in which two or three, but preferably only one, of the cyclic radicals defined above, preferably of the unsubstituted cyclic radicals defined above, is carried by a $C_1$-$C_3$-alkyl radical, all of them preferably being located at one carbon atom, preferably the terminal carbon atom; unsubstituted benzyl is preferred most of all.

Especially preferred compounds of formula I are those in which Ro represents $C_1$-$C_7$-alkyl, especially $C_1$-$C_4$-alkyl, hydroxy-$C_2$-$C_{18}$-alkyl, especially hydroxy-$C_2$-$C_{14}$-alkyl, cyano-$C_1$-$C_7$-alkyl, especially cyano-$C_1$-$C_4$-alkyl, carboxy-$C_1$-$C_7$-alkyl, especially carboxy-$C_1$-$C_4$-alkyl, $C_1$-$C_7$-alkoxycarbonyl-$C_1$-$C_7$-alkyl, especially $C_1$-$C_4$-alkoxycarbonyl-$C_1$-$C_4$-alkyl, benzyloxycarbonyl-$C_1$-$C_7$-alkyl, especially benzyloxycarbonyl-$C_1$-$C_4$-alkyl, $C_3$-$C_7$-alkenyl, phenyl, naphthyl, pyridyl, quinolyl, or quinazolyl, or phenyl-$C_1$-$C_7$-alkyl, especially phenyl-C1-C3-alkyl, it furthermore being possible for the respective aromatic radicals also to be substituted by $C_1$-$C_7$-alkyl, especially $C_1$-$C_4$-alkyl, $C_1$-$C_7$-alkoxy, especially $C_1$-$C_4$-alkoxy, halogen, nitro, trifluoromethyl, also carboxy, $C_1$-$C_4$-alkoxycarbonyl, methylenedioxy and/or by cyano, the hydroxy group in the correspondingly substituted alkyl radical being located especially in the 2-position and the cyano, carboxy, alkoxycarbonyl, benzyloxycarbonyl or phenyl group in the correspondingly substituted alkyl radical being located especially in the 1- or ω-position.

Especially preferred compounds of formula I are those in which $R^o$ represents $C_1$-$C_4$-alkyl, such as methyl or ethyl, hydroxy-$C_2$-$C_{14}$-alkyl, such as 2-hydroxy-propyl, -hexyl, -decyl or -tetradecyl, cyano-$C_1$-$C_4$-alkyl, such as 2-cyanoethyl, carboxy-$C_1$-$C_4$-alkyl, such as carboxymethyl, $C_1$-$C_4$-alkoxycarbonyl-$C_1$-$C_4$-alkyl, such as methoxycarbonyl-methyl or -ethyl, $C_3$-$C_7$-alkenyl, such as allyl, or phenyl, the hydroxy group in the correspondingly substituted alkyl radical being located preferably in the 2-position and the cyano, carboxy or alkoxycarbonyl group being located especially in the 1- or ω-position.

The acyl radical Ac is derived from an optionally functionally modified carboxylic acid, an organic sulphonic acid or an optionally esterified phosphoric acid, such as pyro- or ortho-phosphoric acid, and preferably has a maximum of 30 carbon atoms.

An acyl radical derived from an optionally functionally modified carboxylic acid, which is designated $Ac^1$, is especially one of the partial formula Z—C(=W)— in which W may represent oxygen, sulphur or imino and Z may represent hydrogen, hydrocarbyl Ro, hydrocarbyloxy $R^oO$, an amino group, especially one of the formula

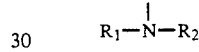

or, if W represents oxygen or sulphur, also chlorine. The meanings of $R^o$, R1 and R2 correspond to the above-mentioned general and preferred meanings, the latter meanings also generally being the preferred choice in this case too.

An acyl radical derived from an organic sulphonic acid, which is designated $Ac^2$, is especially one of the partial formula $R^o$—$SO_2$— in which $R^o$ represents a hydrocarbyl radical with the above-mentioned general and preferred meanings, the latter generally being the preferred choice in this case too.

An acyl radical derived from an optionally esterified phosphoric acid, which is designated $Ac^3$, is especially one of the partial formula

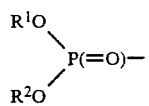

in which $R^1$ and $R^2$ independently have the above-mentioned general and preferred meanings. Preferably, $R^1$ and $R^2$ have the same meaning.

Preferred acyl radicals $Ac^1$ are acyl radicals of a carboxylic acid that are characterised by the partial formula $R_b^o$—CO—, in which $R_b^o$ either represents hydrogen (and thus forms the formyl radical) or has one of the above-mentioned general and preferred meanings of the hydrocarbyl radical $R^o$, and are thus derived from an optionally substituted acyclic, carbocyclic, carbocyclic-acyclic, heterocyclic or heterocyclic-acyclic monocarboxylic acid. A preferred hydrocarbyl radical in such an acyl radical is, for example, a $C_1$-$C_{19}$-alkyl radical, especially a $C_1$-$C_7$- or $C_1$-$C_4$-alkyl radical, especially one that with more than 5 carbon atoms has a linear chain and that also may carry the following substituents: a carboxy group, which may optionally also be in salt form or in the form of a cyano group or a $C_1$-$C_4$-alkyl ester group ($C_1$-$C_4$-alkoxycarbonyl group) and which is preferably in the -position; an amino group of the above-defined formula

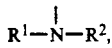

preferably one in which $R^1$ and $R^2$ each represents hydrogen, in which case it is preferably in the 1-position; or one or more halogen atoms, especially fluorine or chlorine, which are preferably adjacent to the carbonyl group. Another preferred acyl radical is a bicyclic or, especially, monocyclic, aroyl radical, especially benzoyl, which may also carry one or more of the following substituents: halogen atoms, especially chlorine or fluorine, nitro groups, $C_1$-$C_4$-alkyl radicals, especially methyl, hydroxy groups and esterified hydroxy groups, especially $C_1$-$C_4$-alkoxy, such as methoxy, phenoxy and methylenedioxy, and also carboxyl groups, which may also be present in salt form or in the form of a cyano group or a $C_1$-$C_4$-alkyl ester group ($C_1$-$C_4$-alkoxycarbonyl group). Preferably, the aroyl radicals carry no more than 2, but especially carry only one, such substituent(s). Also preferred are analogous heteroaroyl radicals, especially those that are derived from pyridine, furan, thiophene and imidazole, and from analogues thereof with a fused benzo ring (such as quinoline, isoquinoline, benzofuran and benzimidazole), and that are optionally also substituted as indicated above. Preferred acyl radicals of this kind are derived also from monocyclic aryl-alkenyl, for example corresponding aryl-$C_2$-$C_5$-alkenyl, such as benzyl and styryl (that is phenacetyl and cinnamoyl), and they may also be substituted in the manner indicated above. Such acyl radicals form with the basic structure of the staurosporine corresponding acylamides, those with the above-mentioned meanings of $Ac^1$ being especially preferred. There may be mentioned by way of example staurosporine amides that are derived from the following carboxylic acids: aliphatic monocarboxylic acids having a maximum of 20 carbon atoms, such as lower alkanecarboxylic acids, for example propionic, butyric, isobutyric, valeric, isovaleric, caproic, trimethylacetic, oenanthic and diethylacetic acid and, especially, acetic acid, and also lauric, myristic, palmitic and stearic acid, as well as oleic acid, elaidic acid, linoleic acid and linolenic acid, but also corresponding halogenated lower alkanecarboxylic acids, such as chloroacetic acid, trifluoro- or trichloroacetic acid, bromoacetic acid or α-bromoisovaleric acid; carbocyclic or carbocyclic-acyclic monocarboxylic acids, for example cyclopropane-, cyclopentane- and cyclohexane-carboxylic acid, or cyclopentaneacetic acid, cyclohexaneacetic acid, cyclopentanepropionic acid and cyclohexanepropionic acid; aromatic carbocyclic carboxylic acids, for example benzoic acid, which may be mono- or poly-substituted in the manner indicated above; aryl- or aryloxy-lower alkanecarboxylic acids and analogues thereof unsaturated in the chain, for example phenylacetic and phenoxyacetic acids, phenylpropionic acids and cinnamic acids each optionally substituted as indicated above for benzoic acid; and heterocyclic acids, for example furan-2-carboxylic acid, 5-tert.-butyl-furan-2-carboxylic acid, thiophene-2-carboxylic acid, nicotinic or isonicotinic acid, 4-pyridinepropionic acid, and pyrrole-2- or -3-carboxylic acids optionally substituted by lower alkyl radicals; and also corresponding α-amino acids, especially naturally occurring α-amino acids of the L series, for example glycine, phenylglycine, alanine, phenylalanine, proline, leucine, serine, valine, tyrosine, arginine, histidine and asparagine, preferably in an N-protected form, that is to say a form in which the amino group is substituted by a conventional amino-protecting group, for example one of those mentioned above; and further, also, dicarboxylic acids, such as oxalic acid, malonic acid, mono- or di-lower alkylmalonic acids, succinic acid, glutaric acid, adipic acid, erucic acid, maleic acid, a phthalo-, quinoline-, isoquinoline- or phenyl-succinic acid each optionally substituted by halogen, such as fluorine, chlorine or bromine, and/or by lower alkyl, hydroxy, lower alkoxy and nitro, as well as, also, glutamic acids and aspartic acid, the last two acids preferably having protected amino groups. As mentioned, the second carboxy group may either be free or functionally modified, for example may be in the form of a $C_1$-$C_4$-alkyl ester or a salt, preferably a physiologically tolerable salt, having a salt-forming basic component. Especially suitable are metal or ammonium salts, such as alkali metal and alkaline earth metal salts, for example sodium, potassium, magnesium or calcium salts, or ammonium salts with ammonia or suitable organic amines.

Another preferred acyl radical $Ac^1$ is derived from monoesters of carbonic acid and is characterised by the partial formula $R^o$—O—CO—. With the basic structure of the staurosporine this acyl radical thus forms corresponding N-disubstituted urethanes. Of the especially preferred hydrocarbyl radicals $R^o$ in these derivatives the following, for example, may be mentioned: acyclic hydrocarbyl, especially a $C_1$-$C_{20}$-alkyl radical, preferably a linear $C_1$-$C_{20}$-alkyl radical that may be substituted by a carboxy group which is preferably in a functionally modified form, such as in the form of a salt, a cyano group or a $C_1$-$C_4$-alkyl ester group, and which is preferably in the ω-position, or an analogous linear (mono- to hexa-) oxaalkyl radical having from 4 to 20 chain members, especially one that has been characterised above as being especially preferred.

Preferred within this meaning of $R_o$ are also optionally substituted phenyl and benzyl radicals, for example those mentioned above as being preferred.

Yet another preferred acyl radical $Ac^1$ is derived from amides of carbonic acid (or also thiocarbonic acid) and is characterised by the formula

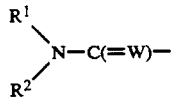

in which $R^1$ and $R^2$ have the meanings given above and W represents sulphur and especially oxygen. With the basic structure of the staurosporine, this acyl radical forms corresponding ureas or thioureas.

Of the preferred compounds of the invention that carry this acyl radical attention is drawn especially to those in which W represents oxygen, one of the radicals $R^1$ and $R^2$ represents hydrogen and the other represents a $C_1$-$C_7$-alkyl radical that may be substituted by hydroxy, mercapto, methylthio, phenyl, p-hydroxyphenyl, p-methoxyphenyl, 2-indolyl, 2-imidazolyl and, especially, by carboxy (free or in a functionally modified form, such as $C_1$-$C_4$-alkoxycarbonyl, carbamoyl or amidino), one of which substituents is located preferably in the 1-position, and that preferably corresponds to a radical of which the free valency is positioned instead of the amino group in a common amino acid, such as β-alanine, γ-aminobutyric acid or norvaline, and especially in an α-amino acid of the L series occurring naturally as a peptide building block, or in an antipode thereof. Attention is drawn also to compounds with acyl of the last-mentioned kind in which W represents sulphur, one of the radicals $R^1$ and $R^2$ represents hydrogen and the other represents a $C_1$-$C_7$-alkyl or especially a $C_1$-$C_7$-alkenyl radical in which the free valency originates from a carbon atom other than the double bond, such as allyl.

Attention is drawn also to compounds of formula I according to the invention in which R represents chloroformyl or thiochloroformyl, which are distinguished especially as advantageous intermediates for the manufacture of modified carbonic acid acyl esters.

The acyl radical $Ac^2$ is derived from an acyclic, carbocyclic or heterocyclic, or also a carbocyclic-acyclic or heterocyclic-acyclic, sulphonic acid and corresponds to the mentioned partial formula $R^o$—$SO_2$— in which $R^o$ represents hydrocarbyl with the above-mentioned general and, especially, preferred meanings. Of the compounds of the invention that carry the radical $Ac^2$, attention is drawn especially to those in which $R^o$ represents a $C_1$-$C_7$-alkyl radical, especially a linear, a bicyclic or especially a monocyclic aryl radical, such as especially phenyl, which may be substituted analogously to that described for preferred aroyl radicals. Attention is drawn also to analogously constructed bicyclic and monocyclic aromatic heterocyclyl radicals in which one or two of the carbon atoms have been replaced by hetero atoms, such as pyrimidyl, for example 2- or 4-pyrimidyl, quinolyl or isoquinolyl. Also the heterocyclyl radicals may carry substituents, especially those specially mentioned for aroyl (in this case, for example a hydroxy derivative is equivalent to a dihydro oxo derivative as a result of tautomeric displacement of the double bond).

The acyl radical $Ac^3$ derived from a phosphoric acid is, for example, such an acyl radical derived from pyrophosphoric acid or, especially, from orthophosphoric acid, which may also be in a functionally modified form, for example in the form of a salt, a hydrocarbyl ester or an amide. Of the compounds of formula I according to the invention in which R represents $Ac^3$, attention is drawn especially to those in which $Ac^3$ corresponds to the partial formula

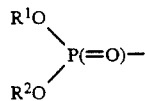

in which $R^1$ and $R^2$ have the above-mentioned general and, especially, preferred meanings, and are preferably the same and represent hydrogen or an unsubstituted $C_1$-$C_7$-alkyl radical, especially a linear such radical, such as, especially, methyl or ethyl, or alternatively a phenyl radical optionally substituted especially by $C_1$-$C_4$-alkyl, $C_1$-$C_4$-alkoxy, halogen atoms and/or by nitro.

Especially preferred are those compounds of formula I in which R represents an acyl radical of the partial formula Z—C(=W)— in which W is oxygen, or also sulphur, and Z represents $C_1$-$C_7$-alkyl, which may also be substituted by halogen, carboxy or by $C_1$-$C_4$-alkoxycarbonyl.

Especially preferred are those compounds of formula I in which R represents an acyl radical of the partial formula Z—C(=W)— in which W is oxygen, or also sulphur, and Z represents phenyl, or also pyridyl, furyl, thienyl, imidazolyl, quinolyl, isoquinolyl, benzofuranyl or benzimidazolyl, each of which is unsubstituted or substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy and/or by cyano.

Especially preferred are those compounds of formula I in which R represents an acyl radical of the partial formula $R_b^o$—CO— in which $R_b^o$ represents $C_1$-$C_7$-alkyl, especially $C_1$-$C_4$-alkyl, such as methyl or tert.-butyl, which may also be substituted by halogen, such as fluorine or chlorine, carboxy or by $C_1$-$C_4$-alkoxycarbonyl, such as methoxycarbonyl, such as trifluoro- or trichloro-methyl and 2-carboxy- or 2-methoxy-carbonylethyl.

Especially preferred are those compounds of formula I in which R represents an acyl radical of the partial formula $R_b^o$—CO— in which $R_b^o$ is phenyl, which may be unsubstituted or also substituted by $C_1$-$C_4$-alkyl, $C_1$-$C_4$-alkoxy, halogen, such as fluorine or chlorine, nitro, trifluoromethyl, carboxy or by $C_1$-$C_4$-alkoxycarbonyl.

Especially preferred are those compounds of formula I in which R represents an acyl radical of the partial formula $R^o$—$SO_2$— in which $R^o$ represents $C_1$-$C_7$-alkyl, especially $C_1$-$C_4$-alkyl.

Especially preferred are those compounds of formula I in which R represents an acyl radical of the partial formula $R^o$—$SO_2$— in which $R^o$ represents phenyl, also pyridyl, furyl, thienyl, imidazolyl, quinolyl, isoquinolyl, benzofuranyl or benzimidazolyl, each of which is unsubstituted or is substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy and/or by cyano.

Especially preferred are those compounds of formula I in which R represents an acyl radical of the partial formula $R^o$—$SO_2$— in which $R^o$ represents phenyl, or phenyl or isoquinolyl, such as 5-isoquinolyl, each substituted by $C_1$-$C_4$-alkyl or by halogen.

Especially preferred are those compounds of formula I in which R represents an acyl radical of the partial formula $R^o$—O—CO— in which $R^o$ represents $C_1$-$C_7$-alkyl, especially $C_1$-$C_4$-alkyl.

Especially preferred are those compounds of formula I in which R represents an acyl radical of the partial formula $R^o$—O—CO— in which $R^o$ represents phenyl, also pyridyl, furyl, thienyl, imidazolyl, quinolyl, isoquinolyl, benzofuranyl or benzimidazolyl, each of which is unsubstituted or is substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy and/or by cyano.

Especially preferred is the compound of formula I in which R represents an acyl radical of the partial formula $R^o$—O—CO— in which $R^o$ represents unsubstituted phenyl.

Especially preferred are those compounds of formula I in which R represents an acyl radical of the partial formula

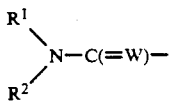

in which W represents sulphur or, especially, oxygen, $R_1$ is hydrogen and $R_2$ represents $C_1$-$C_7$-alkyl, especially $C_1$-$C_4$-alkyl, $C_3$-$C_7$-alkenyl or phenyl, or also pyridyl, furyl, thienyl, imidazolyl, quinolyl, isoquinolyl, benzofuranyl or benzimidazolyl, each of which is unsubstituted or substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy and/or by cyano.

Especially preferred are those compounds of formula I in which R is derived from an α-amino acid, especially a naturally occurring α-amino acid of the L series.

Especially preferred are those compounds of formula I in which R is derived from an α-amino acid selected from glycine, phenylglycine, alanine, phenylalanine, proline, leucine, serine, valine, tyrosine, arginine, histidine, glutamic acid, aspartic acid and asparagine.

Especially preferred are those compounds of formula I in which R is derived from an α-amino acid selected from glycine, alanine, phenylalanine and serine, and also from glutamic acid, aspartic acid, arginina and histidine.

Especially preferred are those compounds of formula I, wherein R represents an acyl radical Ac which is derived from an α-amino acid in which the α-amino group is protected by an amino-protecting group, it being possible for corresponding amino acids which carry a hydroxy radical to have additionally protected the hydroxy group by a hydroxy-protecting group and it being possible for corresponding amino acids which carry an additional carboxy group to have this carboxy group esterified by, for example, a lower alkanol or a phenyl-lower alkanol, such as a 1-phenyl-lower alkanol, or wherein R represents an acyl radical Ac which is derived from an α-amino acid carrying a hydroxy group that is protected by a hydroxy-protecting group, and their salts.

There come into consideration especially corresponding naturally occurring amino acids of the L series.

Especially preferred α-amino acids of the kind defined hereinbefore are glycine, phenylglycine, alamine, phenylalanine, proline, leucine, isoleucine, tyrosine, valine, arginine, histidine, glutamic acid, aspartic acid and asparagine; most preferred are, however, glycine, alamine, phenylalanine and serine, and also glutamic acid and aspartic acid.

Corresponding protecting groups as well as their introduction and removal are described, for example, in "Protective Groups in Organic Chemistry" (Plenum Press, London/New York, 1973), in "Methoden der Organischen Chemie" (Houben-Weyl, 4th edition, Volume 15/1, Georg-Thieme-Verlag, Stuttgart, 1974) and in Theodora W. Greene, "Protective Groups in Organic Synthesis" (John Wiley & Sons, New York, 1981). It is a characteristic feature of protecting groups that they are easily removable, that is to say without the occurrence of undesired side reactions.

There come into consideration as amino-protecting groups especially acyl radicals, preferably acetyl, trifluoroacetyl, tert.-butyloxycarbonyl and benzyloxycarbonyl, and also benzoyl, and as hydroxy-protecting groups preferably benzyl, and also tert.-butyl and acetyl. Corresponding esters of amino acids which carry an additional carboxy group are especially corresponding lower alkyl esters, such as methyl, ethyl and isopropyl esters, and 1-phenyl-lower alkyl esters, such as benzyl esters.

Depending upon their nature, the compounds according to the invention, if they contain salt-forming groups, may also be in the form of salts, especially pharmaceutically acceptable, that is to say physiologically tolerable, salts. For the purpose of isolation or purification it is also possible to use pharmaceutically unsuitable salts. Only pharmaceutically acceptable salts can be used therapeutically and these are preferred.

Thus, for example, a compound having a free acid group, such as, for example, a free sulpho, phosphoryl or carboxy group, especially in the acyl radical Ac, may be in the form of a salt, preferably a physiologically tolerable salt, having a salt-forming basic component. There come into consideration especially metal or ammonium salts, such as alkali metal and alkaline earth metal salts, for example sodium, potassium, magnesium or calcium salts, or ammonium salts with ammonia or suitable organic amines, especially tertiary monoamines and heterocyclic bases, for example triethylamine, tri-(2-hydroxyethyl)-amine, N-ethylpiperidine, or N,N'-dimethylpiperazine. If such an acid group occurs in a hydrocarbyl radical $R^o$, it may also form an internal salt with the amino nitrogen atom of the staurosporine basic structure, or with another amino group that may be present.

Compounds according to the invention of basic character may also be in the form of addition salts, especially acid addition salts with inorganic and organic acids, but also in the form of quaternary salts. Thus, for example, compounds of formula I that carry as substituent in the Ac radical a basic group, such as an amino group, form acid addition salts with common acids. Attention is drawn especially to addition salts of the formula

in which [Stau] and $R^o$ have the meanings given at the beginning, $R_q^o$ represents hydrogen or an unsubstituted, preferably linear, $C_1$-$C_4$-alkyl radical, such as, especially, ethyl or, more especially, methyl, or benzyl, and $X^-$ represents an anion of an inorganic or organic acid or of a carboxy radical present in the radical $R^o$, physiologically tolerable salts being preferred. The quaternary salts of formula IA that are preferred are those in which the first carbon atom in the hydrocarbyl radical $R^o$ is present as methylene.

Inter alia the following common acids, for example, are suitable for the formation of the anion $X^-$: hydrohalic acids, for example hydrochloric and hydrobromic acid, sulphuric acid, phosphoric acid, nitric acid or perchloric acid, or aliphatic, alicyclic, aromatic or heterocyclic carboxylic or sulphonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic acid, embonic acid, methanesulphonic, ethanesulphonic, hydroxyethanesulphonic, ethylenedisulphonic, halobenzenesulphonic, toluenesulphonic and naphthalenesulphonic acids, or sulphanilic acid, and also methionine, tryptophan, lysine or arginine, as well as ascorbic acid. In quaternary salts preferred meanings of X- are anions of strong inorganic acids, such as hydrohalic acids, especially bromides and iodides, or organic sulphonic acids, such as methanesulphonates (mesylates), p-toluene-sulphonates (tosylates), p-bromobenzene-sulphonates (brosylates) and p-nitrobenzenesulphonates.

Especially preferred compounds of formula I and IA are those described in the Examples.

The compounds of formula I according to the invention and salts thereof are manufactured by general processes in organic chemistry that are known per se, especially as follows: staurosporine of the formula [Stau-]—NH—CH$_3$ (III) in which [Stau] has the meaning given above, or an acid addition salt thereof is either a) reacted with a reagent of the formula R—Y (III) in which R has the meanings given above and Y represents an optionally reactively activated hydroxy group or an additional single bond, the other end of which replaces a hydrogen atom in the radical R, or b) to manufacture compounds of formula I in which R represents a radical of the partial formula H—R$_a{}^o$— in which R$_a{}^o$ represents a divalent hydrocarbyl radical of aliphatic character corresponding to the general structure of R$^o$ (that is one in which the functionalised carbon atom is bonded by single bonds to adjacent carbon and/or hydrogen atoms), is reacted with a carbonyl reagent of the formula R$_a{}^o$=O (IV) in which R$_a{}^o$ has the meaning given above, and at the same time or subsequently is reacted with a reducing agent, and, if desired, a resulting compound of formula I is converted into a different compound of formula I and/or a compound of formula I obtained in free form is converted into a salt thereof and/or a compound of formula I obtained in the form of a salt is converted into its free form or into a different salt.

The reaction according to the invention of staurosporine with a reagent of type a), that is to say a reagent of the formula III, is carried out under known process conditions that are generally customary in organic chemistry for the substitution of amines, usually at temperatures between the freezing point and the boiling point of the reaction mixture, such as in a temperature range of from approximately $-10°$ to approximately $+160°$, especially from approximately $+20°$ to approximately $+50°$, under atmospheric or elevated pressure, in heterogeneous phase (such as a suspension) while stirring or shaking, or especially in homogeneous liquid phase, such as in an excess of liquid reagent or, especially, in the presence of solvents, especially organic solvents, and optionally in the presence of acid-binding inorganic or organic agents. Suitable solvents are, for example, aprotic organic solvents of low polarity, such as aliphatic and aromatic hydrocarbons of the type comprising pentane, hexane, heptane and cyclohexane, or benzene, toluene and xylenes, respectively, as well as halogenated, especially chlorinated, aliphatic hydrocarbons, such as chloroform and dichloromethane, and especially polar aprotic solvents, such as aliphatic and cyclic ethers, for example diethyl ether, 1,2-dimethoxyethane and diisopropyl ether, or dioxan and tetrahydrofuran, respectively, lower aliphatic esters and amides, such as ethyl acetate and formamide, acetamide, N,N-dimethylacetamide and dimethylformamide, respectively, and also acetonitrile, dimethyl sulphoxide and hexamethylphosphorus triamide; under certain conditions also water or a protic organic solvent, such as a lower alkanol, for example methanol, ethanol, isopropyl alcohol and tert.-butyl alcohol, as well as glycol or diglycol monoether, for example 2-methoxyethanol, is advantageous as solvent. In this case it is often advantageous to increase the reaction rate by elevated pressure, for example by carrying out the reaction in closed vessels, in order to increase the boiling and reaction temperature. The solvents can also be used in expedient combinations, for example in order to increase the solubility of components.

Suitable acid-binding agents are in principle any basic compounds, such as, on the one hand, organic nitrogen-containing bases, for example tertiary amines of the type comprising triethylamine, ethyldiisopropylamine, N,N-dimethylaniline, N-ethylpiperidine and N,N'-dimethylpiperazine, or aromatic heterocyclic bases of the type comprising pyridine, collidine, quinoline and 4-dimethylaminopyridine, and on the other hand inorganic compounds having a basic reaction, especially alkali metal hydroxides, carbonates and hydrogen carbonates, and also salts of carboxylic acids, such as sodium or potassium acetate.

Finally, this function can also be performed by nitrogen-containing compounds having a neutral reaction, which are also often at the same time advantageous solvents, for example carboxylic acid amides, especially lower aliphatic carboxylic acid amides, such as those mentioned above, and cyclic amides, such as N-methylpyrrolidone, as well as amido derivatives of carbonic acid, such as urethanes and urea.

Although the exchange reaction is always based on the same principle and the reaction is carried out in accordance with a unitary basic scheme, for an optimum result it is necessary in practice to take into account the individual character of the reactants, especially that of the reactant of formula III.

According to the above definition, the radical R may be a hydrocarbyl radical R$^o$ with the above-mentioned general and preferred meanings. In this case Y represents especially a reactive esterified hydroxy group (as a special form of the above-mentioned reactively activated hydroxy group), that is to say one that is esterified by a strong inorganic acid, such as a hydrohalic acid (for example hydrochloric, hydrobromic or hydriodic acid), an oxygen-containing mineral acid, such as phosphoric acid and especially sulphuric acid, or a strong organic, such as aliphatic or aromatic, sulphonic acid (for example methane- and ethane-sulphonic acid, or benzene-, p-toluene-, p-nitrobenzene- and p-chlorobenzene-sulphonic acid, respectively). If R$^o$ is of aliphatic character, that is to say its free valency originates from a carbon atom that is bonded only by single bonds to adjacent carbon or hydrogen atoms, then there is a free choice from among the esterified hydroxy groups mentioned above; if, however, Ro is of aromatic character, that is to say its free valency originates from a carbon atom that is a member of an aromatic carbocyclic or heterocyclic ring, esters of hydrohalic acids, especially bromides and iodides, are preferred.

A reagent of formula III in which Y represents an additional single bond to a hydrocarbyl radical R$^o$ (replacing a hydrogen atom thereof), is, for example, an alkene, especially one in which the double bond is in addition activated by a special structural characteristic, such as in 2-methylpropene, or by substitution, such as especially in acrylonitrile. Included in the definition of Y there is also a single bond of which the other end is bonded not directly to a carbon atom of the hydrocarbyl radical $R^o$, but to a hetero atom occurring as substituent, such as oxygen (that is an oxygen atom of a hydroxy group) or nitrogen (of an amino group) [replacing a hydrogen atom of such a group]; especially preferred are reagents of the formula $R^oY$ that contain the α-epoxide (oxirane) or α-imine (aziridine) grouping and act as an advantageous source of $R^o$ radicals having a 2-hydroxy- or 2-amino-alkyl grouping. The reaction with these reagents is preferably carried out in the presence of lower alkanols at elevated temperature, for example at from approximately +100° to approximately 150° C., and optionally (in order to increase the boiling temperature of the reaction mixture) under elevated pressure, or under basic conditions and especially with an excess of the reagent.

According to the definition given at the beginning, the radical R may represent an acyl radical Ac, especially an acyl radical Ac derived from an amino acid, and accordingly form the basis of an acylation agent of the formula AcY in which both Ac and Y have the general and preferred meanings already mentioned, such as for $Ac^1$, $Ac^2$ and $Ac^3$. Preferably, Y represents halogen, especially chlorine, bromine or iodine.

In acylation agents that are derived from the above-defined acyl radical $Ac^1$ of a carboxylic acid, Y may represent, for example, a reactively activated hydroxy group. Such a group already exists in the free carboxy group of a carboxylic acid of the formula $R^o$—COOH if, as a result of special structural characteristics, such as in trifluoroacetic acid and especially formic acid, it has sufficient reactivity, but especially when it has been activated by the action of activating reagents, for example carbodiimides, such as, especially, dicyclohexylcarbodiimide or di-(2-imidazolyl)-carbodiimide and other analogous compounds, and optionally in the presence of active ester-forming auxiliaries, such as substituted phenols and especially N-hydroxyamino compounds of the type comprising 1-hydroxybenzotriazole, N-hydroxyphthalimids and N-hydroxy-maleinimide and -succinimide.

If the acyl radical Ac is derived, for example, from an α-amino acid or from an N- and/or O-protected derivative thereof, respectively, as defined at the beginning, preferably the corresponding amino acid (R-Y or Ac-Y, respectively; Y=hydroxy) or a salt thereof, especially a salt with a base, is used as starting material and subsequently treated with a customary activating reagent, for example with one of the activating reagents mentioned hereinbefore, it being possible for the carboxy group to be temporarily activated (for example with the formation of the corresponding N-hydroxysuccinimide ester). Advantageously, the reaction is carried out in situ, the activated intermediates not being isolated. Preferred activating reagents are dicyclohexylcarbodiimide and N-hydroxysuccinimide.

An advantageous activated hydroxy group in acyl radicals of any kind, for example in $Ac^1$, $Ac^2$ and $Ac^3$, is a reactive hydroxy group esterified by strong acids, such as that defined above in connection with the hydrocarbyl radical Ro that forms with the acyl radical a mixed acid anhydride. Of these attention is drawn especially to mixed anhydrides with hydrohalic acids, especially with hydrobromic acid and, more especially, hydrochloric acid, that is acid bromides or acid chlorides, for example those of the formulae Z—C(=W)—Hal, $R^o$—SO$_2$—Hal and

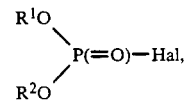

in which Hal represents bromine or preferably chlorine and Z, W, $R^o$, $R^1$ and $R^2$ have the meanings given above; as a special embodiment phosgene and thiophosgene may be mentioned.

In acyl radicals $Ac^1$ of carboxylic acids (including acyl radicals of a functionally modified carbonic acid) the reactive esterified hydroxy group may also be esterified either by the radical of a different carboxylic acid, especially a stronger carboxylic acid, such as formic acid, chloroacetic acid or preferably trifluoroacetic acid, and form the basis of a mixed anhydride, or alternatively may be esterified by the same acyl radical, and form a symmetrical carboxylic acid anhydride of the formula Acl—O—Acl, especially one of the formula $R^o$—CO—O—CO—$R^o$ or $R^o$—O—CO—O—CO—O—$R^o$ (or a sulphur analogue thereof).

Acylations with the above-described acylation agents are preferably carried out in the presence of an acid-binding agent, such as one of those mentioned above, which is especially used in an equivalent amount or a small excess (that does not normally exceed 2 equivalents).

Acylation agents of the formula AcY in which Y represents an additional bond to the radical Ac are derived especially from acyl radicals $Ac^1$ of carboxylic acids, especially those that carry a hydrogen atom at the atom adjacent to the carbonyl group (that is to say at the adjacent carbon or nitrogen atom); they belong to the category of ketenes and isocyanates, respectively, and correspond to the formulae $R_a^o$=C=O and $R^1$—N=C=O respectively, in which $R_a^o$ has the meaning defined above of a divalent hydrocarbyl radical of aliphatic character corresponding to the radical $R_a^o$ and $R^1$ has the above-mentioned general and, especially, preferred meanings with the exception of hydrogen. Mention should also be made of an analogous sulphur-containing isothiocyanate acylation agent of the formula $R^1$—N=C=S in which $R^1$ has the above-mentioned general and preferred meanings except for hydrogen. Acylation with such agents, depending on the nature thereof, can also be carried out without acid-binding agents; a strict exclusion of moisture and/or protic solvents is recommended.

The N- and/or O-protected amino acid derivatives to be used for the preparation of compounds of formula I, wherein R represents an acyl radical which is derived from an α-amino acid in which the α-amino group is protected by an amino-protecting group, it being possible for corresponding amino acids which carry a hydroxy radical to have additionally protected the hydroxy group, or wherein R represents an acyl radical which is derived from an α-amino acid carrying a hydroxy group that is protected by a hydroxy-protecting group, and of their salts are known or can be prepared in a manner known per se, for example according to the procedures described in "Methoden der Organischen Chemie" (Houben-Weyl, 4th edition, Volume 15/1, cited hereinbefore).

Process variant b) is generally known as "reductive alkylation" and frequently used. Carbonyl reagents of the above-defined formula $R_a{}^o=O$ [IV] include especially aldehydes, but also ketones, including cyclic ketones, in which the carbonyl group is a member of an alicyclic ring; these reagents are preferably derived from unsubstituted hydrocarbyl radicals, or at least carry substituents that are resistant to reduction. Suitable reducing agents are complex metal hydrides, such as alkali metal aluminium hydrides and especially alkali metal borohydrides, for example lithiumaluminium hydride, potassium borohydride, lithium borohydride and especially sodium borohydride, and derivatives thereof, in which one or more hydrogen atoms have been replaced by alkoxy radicals or cyano, for example methoxysodium borohydride, tri-(tert.-butoxy)-lithium borohydride or di-(2-methoxyethoxy)-disodium lithium hydride or sodium cyanoborohydride, as well as, also, diborane. These reducing agents are preferably added only in the second phase of the alkylation, that is to say after the primary addition of the carbonyl reagent. Another frequently used reducing agent is elemental hydrogen, which is used under the customary conditions of catalytic hydrogenation, simultaneously with the carbonyl component, at temperatures of from approximately $+20°$ to approximately $+100°$ and, if necessary, an excess pressure of up to approximately 150 atm. The catalyst usually used is Raney nickel, or alternatively palladium or platinum, preferably on an inert carrier, such as calcium carbonate, barium sulphate or aluminium oxide. Another variant of the reductive alkylation uses formic acid as the reducing agent; it is especially suitable for methylation with formaldehyde.

According to the invention, if desired a resulting compound of formula I can be converted into a different compound of formula I; accordingly, especially a functional group present in the radical R is converted into a different functional group, for example a functionally modified, especially a protected, hydroxy, carboxy or amino group is converted into its free form, or a reactive chlorine atom (such as that in the chloroformyl radical) is exchanged for the radical $R^o$—O— or $R^1$—N(—$R^2$)—. Freeing a functionally modified group is, for example, the conversion of an esterified carboxy group into a free carboxy group, which can generally be carried out by conventional hydrolysis, especially under the action of bases (such as especially alkali metal hydroxides, carbonates or hydrogen carbonates) or alternatively, in the case of suitable esters, such as those of tertiary alcohols (for example tert.-butyl alcohol), by acidolysis, for example by means of hydrogen fluoride or trifluoracetic acid. Esters with benzyl alcohols can also be removed by conventional hydrogenolysis. Since esterification is one of the most usual methods of protecting carboxy groups, the above conversion is also an effective method of removing carboxy-protecting groups.

The groups to be used for the temporary protection of hydroxy groups and methods for their removal are also generally known, for example from the synthesis of peptides. In particular hydroxy groups are protected in the form of esters with carboxylic acids, such as with lower alkanoic acids or with monoesters of carboxylic acid (for example formates or acetates on the one hand or tert.-butoxy- or benzyloxy-carbonates on the other hand), or alternatively in the form of ethers, such as especially those of tertiary alcohols (for example tert.-butyl alcohol) or also in the form of acetals (for example especially in the form of 2-tetrahydropyranyl ether). The former protecting groups are customarily removed analogously to esterified carbonyl groups; both of the latter are removed especially by acidolysis.

The protecting groups that can be employed for the temporary protection of primary and secondary amino groups correspond to those that have been examined in detail in the synthesis of peptides and are the most widely used; preferably the amino-protecting groups mentioned at the beginning are used. Their removal, which generally depends on their specific nature, is carried out under generally known conditions of hydrolysis (especially basic hydrolysis), acidolysis or hydrogenolysis.

The general conditions of the conventional removal of the functionally modified groups are especially so selected that neither the bond between the radical R and the methylamino group of the staurosporine nor its basic structure is impaired; since these structural features are generally distinguished by good stability, conventional reaction conditions without special cautionary measures can be used.

In compounds of formula I, wherein R represents an acyl radical which is derived from an $\alpha$-amino acid carrying an amino- and/or a hydroxy-protecting group, the corresponding protecting group can be removed in a manner known per se, for example by catalytic hydrogenolysis, for example in the presence of a noble metal catalyst, such as Pd, Pd/C, Pt or PtO$_2$ (for example for the removal of a benzyloxycarbonyl, benzoyl or benzyl group); by reductive cleaving, for example using Na/NH$_3$ (for example for the removal of a benzyloxycarbonyl or benzyl group); by acidolysis, for example using a hydrohalic acid, optionally in the presence of acetic acid or trifluoroacetic acid (for example for the removal of a benzyloxycarbonyl, tert.-butyloxycarbonyl, trifluoroacetyl, benzyl or tert.-butyl group); or by reductive cleaving using a hydride, which may be in complex form for example NaBH$_4$ (for example for the removal of a trifluoroacetyl group). The reagents to be used for the removal of protecting groups have to be selected in such a way, that a hydroxy-protecting group can be selectively removed in the presence of an amino-protecting group, and vice versa.

Also, in compounds of formula I, which carry a carboxy group as substituent (for example in those compounds, wherein R represents an acyl radical (Ac), which is derived from an optionally protected $\alpha$-amino acid carrying an additional carboxy group), this carboxy group can be converted into an esterified carboxy group, for example by treatment with an alcohol, such as a (phenyl-)lower alkanol, for example in a manner analogous to variant a), such as in the presence of a suitable esterification reagent, for example of an acidic reagent, such as an inorganic or organic acid or a Lewis-acid, for example zinc chloride, or of a water-binding condensation agent, for example a carbodiimide, such as N,N'-dicyclohexylcarbodiimide, or by treatment with a diazo reagent, such as a diazo-lower alkane, for example diazomethane. An esterified carboxy group can also be obtained by treatment of a compound of formula I, wherein the carboxy group is present in free form or in form of a salt, for example as an ammonium- or a metal salt, such as an alkali metal salt, for example a sodium or potassium salt, with a reactive ester of a $C_1$-$C_4$-alkyl halogenide, for example with methyl or ethyl chloride, -bromide or -iodide, or with an ester of an organic sulfonic acid, such as a corresponding $C_1$-$C_7$-alkyl ester, for example with methanesulfonic acid or p-toluenesulfonic acid methyl ester or ethyl ester.

Corresponding compounds of formula I, which carry an esterified carboxy group as substituent, can be transesterified, yielding different ester compounds of formula I, this transesterification being performed, for example, by treatment with an alcohol, customarily with an alcohol higher than the one which corresponds to the -O-alk-group in the esterified carboxy group —C(=O)—O—alk of the starting material, in the presence of a suitable transesterification reagent, such as a basic reagent, for example an alkali metal-lower alkanoate, -lower alkanolate or -cyanide, such as sodium acetate, -methanolate, -ethanolate, -tert.-butanolate or -cyanide, or a suitable acidic reagent, optionally with the removal, for example by distillation, of the alcohol formed. It is also possible to use as starting materials corresponding so-called activated esters of formula I, which carry an activated esterified carboxy group (see below) as substituent, and to transesterify the activated esterified carboxy group by treatment with a lower alkanol, yielding a different ester compound.

It is also possible, in corresponding compounds of formula I, which carry a carboxy group as substituent, to convert first this carboxy group into a reactive derivative, such as an anhydride, inclusive of a mixed anhydride, for example an acid halide, such as an acid chloride (for example by treatment with a thionyl halide, for example thionyl chloride), or an anhydride with a formic acid ester, for example a formic acid lower alkyl ester (for example by treatment of a salt, such as an ammonium or alkaline metal salt, with a halogenoformic acid ester, such as a chloroformic acid ester, for example a halogenoformic acid lower alkyl ester, such as a chloroformic acid lower alkyl ester), or an activated ester, such as a nitrophenyl, for example 4-nitrophenyl, polyhalogenophenyl, for example pentachlorophenyl, or cyanomethyl ester (for example by treatment with a corresponding hydroxy-compound in the presence of a suitable condensation agent, such as N,N'-dicyclohexylcarbodiimide), and subsequently to react the resulting reactive derivative with a corresponding alcohol, thus yielding corresponding compounds of formula I, which carry an esterified carboxy group as substituent. The last-mentioned esters of formula I can be obtained, starting from the reactive derivatives, directly or via intermediates; thus, it is possible, for example, to react an activated ester, such as a 4-nitrophenylester, of a compound of formula I carrying a carboxy group first with an 1-unsubstituted imidazole and subsequently to react the resulting 1-imidazolylcarbonyl compound with the alcohol.

A subsequent conversion of a reactive chlorine atom according to the invention, which can be carried out if desired, occurs especially in the conversion of the chloroformyl group (Cl—CO—) into the hydrocarbyloxycarbonyl group ($R^o$—O—CO—) or aminocarbonyl-(carbamoyl-) group [$R^1$—N(—$R^2$)—CO—]. This conversion is carried out under conditions that are known per se, by reacting N-chloroformylstaurosporine with an alcohol of the formula $R^o$-OH or an amine (including ammonia) of the formula $R^1$—NH—$R^2$, preferably in the presence of an acid-binding agent, such as an organic base (for example one of the tertiary amines mentioned above). The general reaction conditions are analogous to those described in detail above for the reactions with reagents having a reactively esterified hydroxy group (especially for acid chlorides).

The salt formation and freeing of the basic forms of the compounds of formula I from their salts, which are carried out if desired, are effected in a conventional manner generally known per se. For example, carboxy-carrying acyl derivatives of formula I are converted into corresponding salts with bases, especially alkali metal salts, by treatment with a corresponding base, especially a compound having an alkaline reaction, such as a hydroxide, carbonate or bicarbonate; the salts can be converted into free carboxy compounds by acidification, for example with inorganic acids, such as, especially, hydrohalic acids. End products having a basic reaction, for example tertiary and quaternary amines of formulae I and IA respectively, can be converted into their salts with acids, for example by treatment with an acid that is suitable for salt formation, such as one of those mentioned above; conversely, by treatment with agents having a basic reaction, such as with inorganic hydroxides, carbonates and bicarbonates, or organic bases and ion exchangers, such a basic underlying form of a tertiary amine of the formula I is freed.

Suitable compounds of the present invention can also form internal salts, for example by customary acid-basic titration to the neutral point or to the isoelectric point, or quaternary ammonium salts of formula IA, for example by treatment with a quaternising agent corresponding to the radical $R_q^o$, such as a reactive ester of a corresponding hydroxy compound with a strong acid, such as a hydrohalic acid, sulphuric acid or a strong organic sulphonic acid.

These or other salts of the novel compounds, such as, for example, the picrates, can also be used for purifying the resulting compounds by converting the free compounds into salts, isolating the latter and recovering the free compounds from the salts again. Owing to the close relationship between the compounds in free form and in the form of their salts, hereinbefore and hereinafter the free compounds shall also include, where appropriate, the corresponding salts (including quaternary salts).

Certain carbonyl functions can be converted into the corresponding thio form, for example by means of suitable reagents that cause the exchange of O for S. For example, by reaction with the Lawesson reagent [2,4-bis-(4-methoxyphenyl)-2,4-dithioxo-1,3,2,4-dithiadiphosphetan] the oxygen atom can be exchanged for a sulphur atom in compounds of formula I and salts thereof that contain, for example, a carboxamide, ketone or lactone grouping as carbonyl function.

The invention relates also to those forms of the process according to which a compound obtainable as intermediate at any stage of the process is used as starting material and the remaining steps are carried out, or a starting material is used in the form of a derivative, for example a salt, or is formed under the reaction conditions.

Known starting materials or starting materials obtainable by known methods, preferably those that result in the compounds described at the beginning as being especially valuable, are used in the process of the present invention. This invention relates also to novel starting materials, that result in the compounds of the formula I.

In view of the above-described pharmacological properties of the novel compounds, the present invention also includes the use, both prophylactically and therapeutically, of the active ingredients of the invention on their own, optionally together with adjuncts, or in combination with other active substances, for example antibiotics or chemotherapeutics, as compositions for the treatment of diseases in which, as has been described above, cell growth is of importance. When used as medicines, the active ingredients of the invention are administered in prophylactically or curatively effective amounts, preferably in the form of pharmaceutical preparations together with conventional pharmaceutical carriers or adjuncts. For example, daily doses of approximately from 1 to 1000 mg, which in acute cases may be exceeded, are administered to warm-blooded animals with a body weight of approximately 70 kg, depending on the species, body weight, age and individual condition and on the method of administration and especially on the particular syndrome. Accordingly, the invention also includes the corresponding method of medicinal treatment.

The invention furthermore relates to pharmaceutical preparations that contain the compounds of the present invention as active ingredients, and to processes for the manufacture of those preparations.

The pharmaceutical preparations of the invention are, for example, for enteral, such as peroral or rectal, administration, and for parenteral administration, to warm-blooded animals. Corresponding dosage unit forms, especially for peroral administration, for example dragées, tablets or capsules, contain preferably from approximately 5 to 500 mg, especially from approximately 10 to 100 mg, of the active ingredient together with pharmaceutically acceptable carriers or adjuncts.

Suitable carriers are especially fillers, such as sugars, for example lactose, saccharose, mannitol or sorbitol, cellulose preparations and/or calcium phosphates, for example triacalcium phosphate or calcium hydrogenphosphate, also binders, such as starch pastes (using, for example, corn, wheat, rice or potato starch), gelatin, tragacanth, methylcellulose and/or, if desired, disintegrators, such as the above-mentioned starches, and also carboxymethyl starch, crosslinked polyvinylpyrrolidone, agar, alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Dragée cores may be provided with suitable coatings that are optionally resistant to gastric juices, there being used, inter alia, concentrated sugar solutions that may contain gum arabic, talc, polyvinylpyrrolidone, polyethylene glycols and/or titanium dioxide, or lacquer solutions in suitable organic solvents or solvent mixtures or, for the manufacture of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to distinguish between different doses of active ingredient.

Other orally administrable pharmaceutical preparations are dry-filled capsules made of gelating, and also soft sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules the active ingredient is preferably dissolved or suspended in suitable liquids, such as fatty oils, paraffin oil or liquid polyethylene glycols, it also being possible for stabilisers to be added.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material; suitable base materials are, for example, liquid triglycerides, polyethylene glycols or paraffin hydrocarbons.

There are suitable for parenteral administration especially aqueous solutions of active ingredients in water-soluble form, for example in the form of water-soluble salts, or aqueous injection suspensions that contain viscosity-increasing substances, for example sodium carboxymethylcellulose, sorbitol and/or dextran, and optionally stabilisers. The active ingredient may also be in the form of a lyophilisate, optionally together with adjuncts, and may be dissolved before parenteral administration by the addition of suitable solvents.

The pharmaceutical preparations of the present invention can be manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary after the addition of suitable adjuncts, into tablets or dragée cores.

The following Examples illustrate the above-described invention but do not limit the scope thereof in any way. Temperatures are in degrees Celsius.

The nomenclature of the products is derived from the complete structure of staurosporine [Stau]—NH—CH$_3$

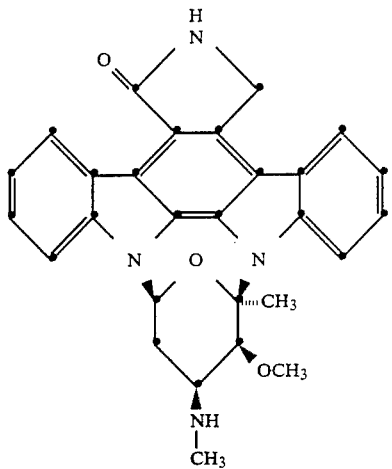

the substituent indicated by N— being positioned at the nitrogen atom of the methylamino group.

EXAMPLE 1

N-methoxycarbonylmethyl-staurosporine 0.056 ml (0.6 mmol) of bromoacetic acid methyl ester is added at room temperature to a mixture of 233 mg (0.5 mmol) of staurosporine, 0.1 ml (0.59 mmol) of N,N-diisopropyl-ethylamine and 2 ml of dimethylformamide. The reaction mixture is stirred in a closed flask for 48 hours at room temperature; the product is precipitated by the addition of 1 ml of water and then recrystallised from methanol. M.p. 210° (decomposition, brown colour from 170°).

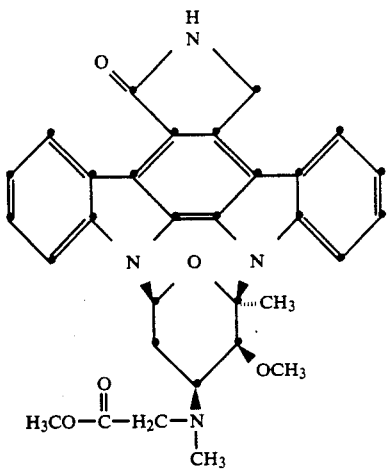

EXAMPLE 2
N-carboxymethyl-staurosporine 269 mg (0.5 mmol) of N-methoxycarbonylmethyl-staurosporine (Example 1) are boiled under reflux for 18 hours in 15 ml of methanol and 0.3 ml of 2N sodium hydroxide solution. After having been cooled to room temperature the reaction mixture is neutralised with 0.1 ml of acetic acid and the product is precipitated by the addition of 15 ml of water. M.p. >230° (decomposition, brown colour from approximately 220°).

EXAMPLE 3
N-(1-methoxycarbonylethyl)-staurosporine 0.085 ml (0.75 mmol) of α-bromopropionic acid methyl ester is added at room temperature to a mixture of 233 mg (0.5 mmol) of staurosporine, 0.12 ml (0.71 mmol) of N,N-diisopropyl-ethylamine and 2 ml of di-methylformamide. The reaction mixture is stirred for 20 hours at room temperature in a closed flask. After the addition of a further 0.044 ml (0.038 mmol) of α-bromopropionic acid methyl ester, the reaction mixture is heated for a further 20 hours at 80° and cooled to room temperature; the product is precipitated by the addition of 2 ml of water. The crude product is purified by chromatography on silica gel (eluant: methylene chloride/ethanol 9:1). M.p. ~150° (decomposition).

EXAMPLE 4
N-benzyl-staurosporine 0.048 ml (0.38 mmol) of benzyl bromide is added at room temperature to a mixture of 116.5 mg (0.25 mmol) of staurosporine, 0.06 ml (0.35 mmol) of N,N-diisopropyl-ethylamine and 1 ml of dimethylformamide and the reaction mixture is stirred at room temperature for 6 hours in a closed flask. The product is precipitated by the addition of 1 ml of water, filtered off and recrystallised from methanol. M.p. ~170° (decomposition).

EXAMPLE 5
N-allyl-staurosporine 0.032 ml (0.38 mmol) of allyl bromide is added at room temperature to a mixture of 116.5 mg (0.25 mmol) of staurosporine, 0.06 ml (0.35 mmol) of N,N-diisopropyl-ethylamine and 1 ml of dimethylformamide and the reaction mixture is stirred at room temperature for 6 hours in a closed flask. The product is precipitated by the addition of 1 ml of water and filtered off. The purification is carried out by chromatography on silica gel with methylene chloride/ethanol 9:1 as eluant. M.p. 160° (decomposition).

EXAMPLE 6
N,N-dimethyl-staurosporinium iodide 0.046 ml (0.75 mmol) of methyl iodide is added at room temperature to a mixture of 233 mg (0.5 mmol) of staurosporine, 0.12 ml (0.71 mmol) of N,N-diisopropyl-ethylamine and 2 ml of dimethylformamide and the reaction mixture is stirred at room temperature in a closed flask. After approximately 1 hour a precipitate forms. After the addition of a further 0.023 ml (0.038 mmol) of methyl iodide and 0.06 ml (0.038 mmol) of N,N-diisopropyl-ethylamine, the reaction mixture is stirred for a further 4 hours at room temperature and, after the addition of 2 ml of water, filtered; the solid crude product is suspended in warm methanol and, after having been cooled, is filtered again and dried. M.p. 260° (decomposition).

EXAMPLE 7
N-ethyl-staurosporine 0.029 ml (0.38 mmol) of ethyl iodide is added at room temperature to a mixture of 116.5 mg (0.25 mmol) of staurosporine, 0.06 ml (0.35 mmol) of N,N-diisopropyl-ethylamine and 2 ml of dimethylformamide and the reaction mixture is stirred at room temperature for 24 hours in a closed flask. The product is precipitated by the addition of 2 ml of water and filtered off. M.p. 170° (decomposition).

EXAMPLE 8
N,N-ethyl-methyl-staurosporinium iodide 0.018 ml (0.3 mmol) of methyl iodide is added at room temperature to a mixture of 115 mg (0.2 mmol) of N-ethyl-staurosporine (Example 7) and 2 ml of dimethylformamide. After 16 hours at room temperature and 16 hours at 50° a further 0.018 ml (0.3 mmol) of methyl iodide is added and the reaction mixture is stirred for 6 hours at 80°. The crude product is obtained by precipitation with 2 ml of water and is recrystallised from dimethylformamide/chloroform. M.p. 265° (decomposition).

EXAMPLE 9
N-(2-hydroxyhexyl)-staurosporine

A suspension of 116.5 mg (0.25 mmol) of staurosporine and 0.054 ml (0.45 mmol) of 1-hexene oxide in 3.5 ml of absolute ethanol is heated at 110° for 36 hours in a Carius tube. The cooled reaction mixture is diluted with water and extracted with methylene chloride. The organic phase is dried over magnesium sulphate, concentrated by evaporation and chromatographed on silica gel (eluant: methylene chloride/ethanol 9:1); recrystallisation from ether/petroleum ether yields the product with a melting point of 110° (decomposition).

EXAMPLE 10

N-(2-hydroxytetradecyl)-staurosporine

A suspension of 116.5 mg (0.25 mmol) of staurosporine and 0.075 ml (0.30 mmol) of 1-tetradecene oxide in 3.5 ml of absolute ethanol is heated at 110° for 68 hours in a Carius tube. The cooled reaction mixture is diluted with water and extracted with methylene chloride. The organic phase is dried over magnesium sulphate, concentrated by evaporation and chromatographed on silica gel (eluant: methylene chloride/ethanol 9:1). Recrystallisation from ether/petroleum ether yields the product with a melting point of 120° (decomposition).

EXAMPLE 11

N-(2-hydroxydecyl)-staurosporine

A suspension of 116.5 mg (0.25 mmol) of staurosporine and 0.055 ml (0.30 mmol) of 1-decene oxide in 3.5 ml of absolute ethanol is heated at 110° for 43 hours in a Carius tube. The cooled reaction mixture is diluted with water and extracted with methylene chloride. The organic phase is dried over magnesium sulphate, concentrated by evaporation and chromatographed on silica gel (eluant: methylene chloride/ethanol 9:1); recrystallisation from ether/petroleum ether yields the product with a melting point of 140°.

EXAMPLE 12

N-(2-cyanoethyl)-staurosporine

A suspension of 116.5 mg (0.25 mmol) of staurosporine in 2.5 ml (38 mmol) of acrylonitrile is heated at 140° for 70 hours in a Carius tube. After having been cooled, the reaction mixture is concentrated by evaporation and chromatographed on silica gel (eluant: methylene chloride/ethanol 9:1). Recrystallisation from chloroform/methanol yields the product with a melting point of ~210°.

EXAMPLE 13

N-acetyl-staurosporine 0.03 ml (0.3 mmol) of acetic acid anhydride is added at room temperature to a solution of 116.5 mg (0.25 mmol) of staurosporine and 0.065 ml (0.38 mmol) of N,N-diisopropylethylamine in 2 ml of chloroform and the whole is stirred for 2 hours in a closed flask. The reaction mixture is diluted with chloroform, washed with sodium bicarbonate solution, dried over magnesium sulphate and concentrated by evaporation. The product is recrystallised from chloroform/methanol; m.p. 240°.

EXAMPLE 14

N-(3-carboxypropionyl)-staurosporine 40 mg (0.4 mmol) of succinic acid anhydride are added at room temperature to a solution of 116.5 mg (0.25 mmol) of staurosporine and 0.065 ml (0.38 mmol) of N,N-diisopropylethylamine in 2 ml of chloroform and the whole is stirred for 28 hours in a closed flask. The reaction mixture is diluted with chloroform, washed with 0.1N hydrochloric acid solution, dried over magnesium sulphate and concentrated by evaporation. The crude product is chromatographed on silica gel (eluant: methylene chloride/ethanol 9:1); m.p. 140°.

EXAMPLE 15

N-(5-isoquinolinesulphonyl)-staurosporine 105 mg (0.4 mmol) of 5-isoquinolinesulphonyl chloride are added at room temperature to a solution of 116.5 mg (0.25 mmol) of staurosporine and 0.118 ml (0.69 mmol) of N,N-diisopropyl-ethylamine in 2 ml of chloroform and the whole is stirred for 29 hours in a closed flask. The reaction mixture is diluted with chloroform, washed with sodium bicarbonate solution, dried over magnesium sulphate and concentrated by evaporation. The product is recrystallised from chloroform/methanol. M.p. 240° (decomposition).

EXAMPLE 16

N-methylsulphonyl-staurosporine 0.023 ml (0.38 mmol) of methanesulphochloride is added at room temperature to a solution of 116.5 mg (0.25 mmol) of staurosporine and 0.065 ml (0.38 mmol) of N,N-diisopropylethylamine in 2 ml of chloroform and the whole is stirred for 24 hours in a closed flask. The reaction mixture is diluted with chloroform, washed with sodium bicarbonate solution, 1N hydrochloric acid and saturated sodium chloride solution, dried over magnesium sulphate and concentrated by evaporation. The crude product is chromatographed on silica gel (eluant: methylene chloride/ethanol 9:1) and recrystallised from chloroform/methanol; m.p. 230°.

EXAMPLE 17

N-(p-tosyl)-staurosporine 57 mg (0.3 mmol) of p-toluenesulphochloride are added at room temperature to a solution of 116.5 mg (0.25 mmol) of staurosporine and 0.065 ml (0.38 mmol) of N,N-diisopropylethylamine in 2 ml of chloroform and the whole is stirred for 68 hours in a closed flask. The reaction mixture is diluted with chloroform, washed with sodium bicarbonate solution, dried over magnesium sulphate and concentrated by evaporation. The crude product is chromatographed on silica gel (eluant: methylene chloride/ethanol 9:1) and recrystallised from chloroform/methanol; m.p. 245°.

EXAMPLE 18

N-benzoyl-staurosporine 0.035 ml (0.3 mmol) of benzoyl chloride is added at room temperature to a solution of 116.5 mg (0.25 mmol) of staurosporine and 0.065 ml (0.38 mmol) of N,N-diisopropylethylamine in 2 ml of chloroform and the whole is stirred for 10 minutes. The reaction mixture is diluted with chloroform, washed with sodium bicarbonate solution, dried over magnesium sulphate and concentrated by evaporation. The crude product is chromatographed on silica gel (eluant:methylene chloride/ethanol 30:1); m.p. 235°-247° with colour turning brown.

EXAMPLE 19

N-trifluoroacetyl-staurosporine 0.5 ml (3.57 mmol) of trifluoroacetic acid anhydride is added at room temperature to a solution of 233 mg (0.5 mmol) of staurosporine and 0.13 ml (0.6 mmol) of N,N-diisopropyl-ethylamine in 2 ml of chloroform and the whole is stirred for 15 minutes. The reaction mixture is diluted with chloroform, washed with sodium bicarbonate solution, dried over magnesium sulphate and concentrated by evaporation. The crude product is chro-

EXAMPLE 20

N-phenoxycarbonyl-staurosporine 0.035 ml (0.28 mmol) of chloroformic acid phenyl ester is added at room temperature to a solution of 116.5 mg (0.25 mmol) of staurosporine and 0.065 ml (0.38 mmol) of N,N-diisopropylethylamine in 2 ml of chloroform and the whole is stirred for 30 minutes in a closed flask. The reaction mixture is diluted with chloroform, washed with sodium bicarbonate solution, dried over magnesium sulphate and concentrated by evaporation. The residue is triturated with hot methanol and, after having been cooled, is filtered and dried. M.p. >210° (decomposition).

EXAMPLE 21

N-methoxycarbonyl-staurosporine 0.025 ml (0.32 mmol) of chloroformic acid methyl ester is added at room temperature to a solution of 116.5 mg (0.25 mmol) of staurosporine and 0.065 ml (0.38 mmol) of N,N-diisopropyl-ethylamine in 2 ml of chloroform and the whole is stirred for 1 hour in a closed flask. The reaction mixture is diluted with chloroform, washed with sodium bicarbonate solution, dried over magnesium sulphate and concentrated by evaporation. The crude product is recrystallised from methanol; m.p. >220° (decomposition).

EXAMPLE 22

N-allylaminothiocarbonyl-staurosporine
(N-allylthiocarbamoylstaurosporine)

0.029 ml (0.3 mmol) of allyl isothiocyanate is added to a solution of 116.5 mg (0.25 mmol) of staurosporine in 2.5 ml of chloroform and the whole is stirred at room temperature for 12 hours in a closed flask. The reaction mixture is concentrated by evaporation and the crude product is recrystallised from chloroform/methanol; m.p. 220°.

EXAMPLE 23

N-methylaminothiocarbonyl-staurosporine
(N-methylthiocarbamoyl-staurosporine)

0.022 mg (0.3 mmol) of methyl isothiocyanate is added to a solution of 116.5 mg (0.25 mmol) of staurosporine in 2.5 ml of chloroform and the whole is stirred at room temperature for 12 hours in a closed flask. The reaction mixture is concentrated by evaporation and the crude product is recrystallised from chloroform/methanol; m.p. 235°–238°.

EXAMPLE 24

N-phenylcarbamoyl-staurosporine 0.033 ml (0.3 mmol) of phenyl isocyanate is added to a solution of 116.5 mg (0.25 mmol) of staurosporine in 2.5 ml of chloroform and the whole is stirred at room temperature for 15 minutes. The reaction mixture is concentrated by evaporation and the crude product is recrystallised from chloroform/methanol; m.p. 225°–229° (brown colour).

EXAMPLE 25

N-trichloroacetyl-staurosporine 0.04 ml (0.35 mmol) of trichloroacetyl chloride is added at room temperature to a solution of 116.5 mg (0.25 mmol) of staurosporine and 0.1 ml (0.58 mmol) of N,N-diisopropyl-ethylamine in 1 ml of chloroform and the whole is stirred for 1 hour. The reaction mixture is diluted with methylene chloride, washed with sodium bicarbonate solution, dried over magnesium sulphate and concentrated by evaporation.

The crude product is chromatographed on silica gel (eluant ethyl acetate); IR: 1682 (strong); FAB-MS: 611.

EXAMPLE 26

N-(3-chlorobenzoyl)-staurosporine 0.038 ml (0.38 mmol) of 3-chlorobenzoyl chloride is added at room temperature to a solution of 116.5 mg (0.25 mmol) of staurosporine and 0.065 ml (0.38 mmol) of N,N-diisopropyl-ethylamine in 2 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 240° (decomposition).

EXAMPLE 27

N-(2-chlorobenzoyl)-staurosporine 0.038 ml (0.38 mmol) of 2-chlorobenzoyl chloride is added at room temperature to a solution of 116.5 mg (0.25 mmol) of staurosporine and 0.065 ml (0.38 mmol) of N,N-diisopropyl-ethylamine in 2 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 255° (decomposition).

EXAMPLE 28

N-(3-nitrobenzoyl)-staurosporine 55.5 mg (0.30 mmol) of 3-nitrobenzoyl chloride are added at room temperature to a solution of 116.5 mg (0.25 mmol) of staurosporine and 0.065 ml (0.38 mmol) of N,N-diisopropyl-ethylamine in 2 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 230°.

EXAMPLE 29

N-(4-methoxybenzoyl)-staurosporine 0.083 ml (0.38 mmol) of a 58% 4-methoxybenzoyl chloride solution in toluene is added at room temperature to a solution of 116.5 mg (0.25 mmol) of staurosporine and 0.065 ml (0.38 mmol) of N,N-diisopropylethylamine in 2 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation. The crude product is chromatographed

EXAMPLE 30

N-(4-fluorobenzoyl)-staurosporine 0.036 ml (0.30 mmol) of 4-fluorobenzoyl chloride is added at room temperature to a solution of 116.5 mg (0.25 mmol) of staurosporine and 0.065 ml (0.38 mmol) of N,N-diisopropyl-ethylamine in 2 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 225° (decomposition).

EXAMPLE 31

N-(4-chlorobenzoyl)-staurosporine 0.077 ml (0.6 mmol) of 4-chlorobenzoyl chloride is added at room temperature to a solution of 233 mg (0.5 mmol) of staurosporine and 0.13 ml (0.76 mmol) of N,N-diisopropyl-ethylamine in 4 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 220° (decomposition).

EXAMPLE 32

N-(3-fluorobenzoyl)-staurosporine 0.072 ml (0.6 mmol) of 3-fluorobenzoyl chloride is added at room temperature to a solution of 233 mg (0.5 mmol) of staurosporine and 0.13 ml (0.76 mmol) of N,N-diisopropyl-ethylamine in 4 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 240° (decomposition).

EXAMPLE 33

N-(4-nitrobenzoyl)-staurosporine 0.11 ml (0.6 mmol) of 4-nitrobenzoyl chloride is added at room temperature to a solution of 233 mg (0.5 mmol) of staurosporine and 0.13 ml (0.76 mmol) of N,N-diisopropyl-ethylamine in 4 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 255°.

EXAMPLE 34

N-(4-methoxycarbonylbenzoyl)-staurosporine 237 mg (1.2 mmol) of 4-methoxycarbonylbenzoyl chloride are added at room temperature to a solution of 466 mg (1 mmol) of staurosporine and 0.26 ml (1.52 mmol) of N,N-diisopropyl-ethylamine in 8 ml of chloroform and the whole is stirred for 1 hour at room temperature. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. 240° (decomposition).

EXAMPLE 35

N-thiobenzoyl-staurosporine

A mixture of 180 mg (0.31 mmol) of N-benzoyl-staurosporine (Example 18) and 132 mg (0.326 mmol) of Lawesson's reagent (Fluka AG) in 2 ml of toluene is stirred at room temperature for 48 hours. For working up, the reaction mixture is diluted with methylene chloride, washed with saturated sodium bicarbonate solution and saturated sodium chloride solution, dried over magnesium sulphate and concentrated by evaporation. The crude product is chromatographed on silica gel (eluant ethyl acetate); FD-MS: 586; H-NMR (300 MHz in CDCl3): 2.99 s.(3H); 2.62 s (3H); 2.56 s (3H).

EXAMPLE 36

N-tert.-butoxycarbonyl-staurosporine

A solution of 65 mg (0.297 mmol) of di-tert.-butyl dicarbonate in 1 ml of tetrahydrofuran is added at room temperature to a solution of 116.5 mg (0.25 mmol) of staurosporine in 2 ml of tetrahydrofuran and the whole is stirred for 9 hours. The reaction mixture is concentrated by evaporation and chromatographed on silica gel (eluant methylene chloride/ethanol 95:5); m.p. 160°.

EXAMPLE 37

N-(4-carboxybenzoyl)-staurosporine sodium salt

A mixture of 314 mg (0.5 mmol) of N-(4-methoxycarbonylbenzoyl)-staurosporine (Example 34), 10 ml of methanol and 0.3 ml of 2N sodium hydroxide solution is heated under reflux for 24 hours. After having been cooled, the reaction mixture is filtered, diluted with 10 ml of water and neutralised with 0.1 ml of acetic acid, during the course of which the title compound is precipitated in the form of an acid (m.p. 275°). For the manufacture of the sodium salt, the acid is suspended in 10 ml of methanol and one equivalent (5 ml) of a 0.1N sodium hydroxide solution is added. The resulting solution is concentrated by evaporation and the residue is recrystallised from methanol/ether; FAB-MS: 637 (M+M)+; 659 (M+Na)+.

EXAMPLE 38

N-(3,5-dinitrobenzoyl)-staurosporine 138 mg (0.6 mmol) of 3,5-dinitrobenzoyl chloride are added at room temperature to a solution of 233 mg (0.5 mmol) of staurosporine and 0.13 ml (0.76 mmol) of N,N-diisopropyl-ethylamine in 4 ml of chloroform and the whole is stirred for 1 hour. The reaction mixture is diluted with chloroform, washed with sodium bicarbonate solution, 1N hydrochloric acid and saturated sodium chloride solution, dried over magnesium sulphate and concentrated by evaporation.

The crude product is chromatographed on silica gel (eluant:methylene chloride/ethanol 95:5); m.p. ~250° (decomposition).

EXAMPLE 39

N-[(tert.-butoxycarbonylamino)-acetyl]-staurosporine 264 mg (1.5 mmol) of BOC-glycine (Fluka AG) and 340 mg (1.65 mmol) of dicyclohexylcarbodiimide are added to 699 mg (1.5 mmol) of staurosporine in 40 ml of dry chloroform and the whole is stirred at room temperature for 1.5 hours. The reaction mixture is then diluted with chloroform, washed with sodium bicarbonate solution and saturated sodium chloride solution, dried over magnesium sulphate and concentrated by evaporation. The residue is suspended in a small amount of methylene chloride and filtered (removal of the dicyclohexylurea). The filtrate is concentrated by evaporation and dried; m.p. 190°.

EXAMPLE 40

N-(2-aminoacetyl)-staurosporine 1 ml of a saturated solution of hydrochloric acid in ethyl acetate is added at room temperature to a solution of 187 mg (0.3 mmol) of N-[(tert.-butoxycarbonylamino)-acetyl]-staurosporine (Example 39) in 1 ml of ethyl acetate. A precipitate is immediately formed. The suspension is subsequently stirred for 10 hours and the product is filtered off and washed with ethyl acetate; m.p. 280° (decomposition).

EXAMPLE 41

N-(2-hydroxy-propyl)-staurosporine

A mixture of 23,3 mg (50 μmol) of staurosporine in 1 ml of dioxane, 0.5 ml (0,05M) of borate buffer (pH 10.0) and 100 μl (1.5 mmol) of propylenoxide is stirred for 13 days. The mixture is extracted twice with dichloromethane and dried over $Na_2SO_4$ with solvent being removed in vacuo. The product is further purified by semi-preparative HPLC (Lichrosorb Si 60, 5 μm, 8×250 μm) using water saturated dichloromethane/2-propanol (98:2, v/v) at a flow rate of 5 ml/min and using detection at 295 nm. Twenty injections are made. The retension time of the product is 15.4 min. The structure is ascertained by EL-MS and $^1$H-NMR (360 Hz).

EXAMPLE 42

N-phenyl-staurosporine

A solution of 2,4 mg (51 μmol) of staurosporine in 0.5 ml of dioxane and 50 μl 1N phenyldiazonium chloride solution (Organikum, 13 ed., Deutscher Verlag der Wissenschaften, Berlin 1974, p. 583) is stirred for 1 hour and poured into a mixture of 1 ml of 2N $NaHCO_3$, 50 ml of dichloromethane and 5 ml of methanol. The organic phase is dried over $Na_2SO_4$, the solvent removed, and the product is then purified by semi-preparative HPLC under the conditions of example 1. The retension time of the product is 5.1 min. The structure is ascertained by EL-MS and $^1$H-NMR (360 Hz).

EXAMPLE 43

N-[(2S)-2-(tert.-butyloxycarbonylamino)-3-phenyl-propionyl]-staurosporine 66 mg (0.25 mmol) of N-BOC-L-phenylalanine and 56.5 mg (0.275 mmol) of dicyclohexylcarbodiimide are added to a solution of 116 mg (0.25 mmol) of staurosporine in 5 ml of dry trichloromethane. The reaction mixture is stirred for 3 hours at room temperature, then diluted with trichloromethane, washed in succession with sodium hydrogencarbonate solution and saturated sodium chloride solution, dried over magnesium sulphate and evaporated to dryness. The residue is chromatographed on silica gel, using dichloromethane/ethanol (95:5) as eluent. The title compound has a melting point of 195°–197°.

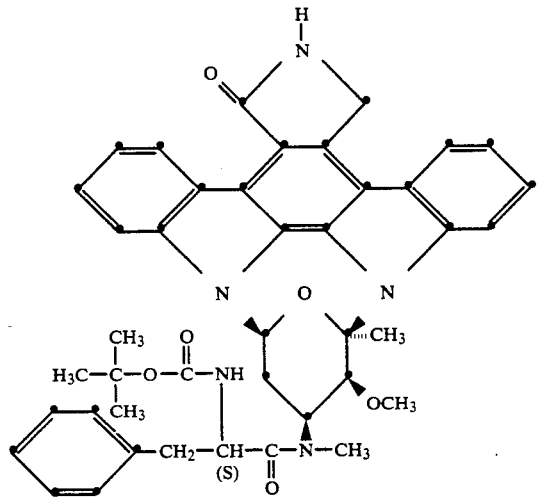

EXAMPLE 44

N-[(2S)-2-(tert.butyloxycarbonylamino)propionyl]-staurosporine 47.5 mg (0.25 mmol) of N-BOC-L-alanine and 56.5 mg (0.275 mmol) of dicyclohexylcarbodiimide are added to a solution of 116 mg (0.25 mmol) of staurosporine in 5 ml of dry trichloromethane. The reaction mixture is stirred for 4 hours at room temperature, then diluted with trichloromethane, washed in succession with sodium hydrogencarbonate solution and saturated sodium chloride solution, dried over magnesium sulphate and evaporated to dryness. The residue is chromatographed on silica gel, using dichloromethane/ethanol (95:5) as eluent. The title compound has a melting point of circa 220° (decomposition).

EXAMPLE 45

N-[(2S)-2-(tert.-butyloxycarbonylamino)-3-benzyloxypropionyl]staurosporine 98 mg (0.25 mmol) of N-BOC-O-benzyl-L-serine-N-hydroxysuccinimide ester (Bachem) are added to a solution of 116 mg (0.25 mmol) of staurosporine in 10 ml of 1,2-dichloroethane. The reaction mixture is stirred in a bomb tube for 12 hours at 110°, then cooled to room temperature and evaporated to dryness. The residue is chromatographed on silica gel, using dichloromethane/ethanol (95:5) as eluent. The title compound has a melting point of 216°–220°.

EXAMPLE 46

N-(acetaminoacetyl)staurosporine 30 mg (0.25 mmol) of N-acetylglycine and 56.5 mg (0.275 mmol) of dicyclohexylcarbodiimide are added to a solution of 116 mg (0.25 mmol) of staurosporine in 10 ml of dry trichloromethane. The reaction mixture is stirred for 2 hours at room temperature and then warmed to reflux for 3.5 hours. Subsequently, another 30 mg (0.25 mmol) of N-acetylglycine and another 56.6 mg (0.275 mmol) of dicyclohexylcarbodiimide are added to the mixture, which is then stirred for further 12 hours at room temperature, then diluted with trichloromethane, washed in succession with sodium hydrogencarbonate solution and saturated sodium chloride solution, dried over magnesium sulphate and evaporated to dryness. The residue is chromatographed on silica gel, using dichloromethane/ethanol (95:5) as eluent. The title compound has a melting point of 235°–240° (decomposition).

EXAMPLE 47

N-(trifluoroacetylaminoacetyl)staurosporine 43 mg (0.25 mmol) of N-(trifluoroacetyl)glycine and 56.5 mg (0.275 mmol) of dicyclohexylcarbodiimide are added to a solution of 116 mg (0.25 mmol) of staurosporine in 10 ml of dry trichloromethane. The reaction mixture is stirred for 1.5 hours at room temperature. Subsequently, another 3 ml of trichloromethane, another 43 mg (0.25 mmol) of N-(trifluoroacetyl)-glycine and another 56.5 mg (0.275 mmol) of dicyclohexylcarbodiimide are added to the mixture, which is then stirred for further 14 hours at room temperature, then diluted with trichloromethane, washed in succession with sodium hydrogencarbonate solution and saturated sodium chloride solution, dried over magnesium sulphate and evaporated to dryness. The residue is suspended in a small volume of dichloromethane and the urea is filtered off. The filtrate is evaporated and the residue is chromatographed, using dichloromethane/ethanol (98:2) as eluent. The title compound has a melting point of 190°–200°.

EXAMPLE 48

N-(benzyloxycarbonylaminoacetyl)staurosporine 52 mg (0.25 mmol) of N-(benzyloxycarbonyl)glycine and 56.5 mg (0.275 mmol) of dicyclohexylcarbodiimide are added to a solution of 116 mg (0.25 mmol) of staurosporine in 10 ml of dry trichloromethane. The reaction mixture is stirred for 1.5 hours at room temperature, then diluted with trichloromethane, washed in succession with sodium hydrogencarbonate solution and saturated sodium chloride solution, dried over magnesium sulphate and evaporated to dryness. The residue is chromatographed on silica gel, using dichloromethane/ethanol (95:5) as eluent. The title compound has a melting point of 185°–193°.

EXAMPLE 49

N-(O-benzyl-L-seryl)staurosporine hydrochloride 2 ml of ethyl acetate, which is saturated with hydrogen chloride, are added at room temperature to a solution of 0.2 g (0.3 mmol) N-(N'-BOC-O-benzyl-L-seryl)-staurosporine (example 45) in 2 ml of ethyl acetate. The title compound precipitates slowly as the reaction proceeds. After a reaction time of 12 hours the product is filtered off, washed with ethyl acetate and dried in a high vacuum (melting point: 230°–235°).

EXAMPLE 50

In a manner analogous to that described in examples 43 to 49 there can also be prepared a) N-[(2S)-2-(tert.-butyloxycarbonylamino)-4-benzyloxycarbonyl-butyryl]staurosporine [by reacting staurosporine with N-BOC-L-glutamic acid-γ-benzyl ester-α-N-hydroxysuccinimide ester (Bachem)];

b) N-[(2S)-2-(tert.-butyloxycarbonylamino)-4-carboxybutyryl]staurosporine and the sodium salt thereof [by basic hydrolysis of the compound prepared in part a)];

c) N-[(2S)-2-(tert.-butyloxycarbonylamino)-3-benzyloxycarbonyl-propion-yl]staurosporine [by reacting staurosporine with N-BOC-L-aspartic acid-β-benzyl ester-α-N-hydroxysuccinimide ester (Bachem)]; and d) N-[(2S)-2-(tert.-butyloxycarbonylamino)-3-carboxypropionyl]staurosporine and the sodium salt thereof [by basic hydrolysis of the compound prepared in part c)].

EXAMPLE 51

The following can be produced in a manner analogous to that described in one of the above Examples:

N-alanyl-staurosporine,
N-arginyl-staurosporine,
N-phenylalanyl-staurosporine,
N-histidyl-staurosporine,
N-seryl-staurosporine.

EXAMPLE 52

Tablets containing 20 mg of active ingredient, for example N-methoxycarbonylmethyl-staurosporine, are manufactured in customary manner with the following composition:

| Composition: | |
| --- | --- |
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Manufacture

The active ingredient is mixed with a portion of the wheat starch, with the lactose and the colloidal silica and the mixture is passed through a sieve. Another portion of the wheat starch is made into a paste with 5 times the amount of water on a water bath and the pulverulent mixture is kneaded with this paste until a slightly plastic mass is obtained.

The plastic mass is pressed through a sieve having a mash width of approximately 3 mm, dried and the resulting dry granulate is passed through a sieve again. The remainder of the wheat starch, the talc and the magnesium stearate are then admixed and the mixture is compressed into tablets with a breaking notch each weighing 145 mg.

EXAMPLE 53

Tablets containing 1 mg of active ingredient, for example N-methoxycarbonylmethyl-staurosporine, are manufactured in customary manner with the following composition:

| Composition: | |
| --- | --- |
| active ingredient | 1 mg |
| wheat starch | 60 mg |
| lactose | 50 mg |

| -continued |  |
| --- | --- |
| Composition: |  |
| colloidal silica | 5 mg |
| talc | 9 mg |
| magnesium stearate | 1 mg |
|  | 126 mg |

Manufacture

The active ingredient is mixed with a portion of the wheat starch, with the lactose and the colloidal silica and the mixture is passed through a sieve. Another portion of the wheat starch is made into a paste with 5 times the amount of water on a water bath and the pulverulent mixture is kneaded with this paste until a slightly plastic mass is obtained.

The plastic mass is pressed through a sieve having a mesh width of approximately 3 mm, dried and the resulting dry granulate is passed through a sieve again. The remainder of the wheat starch, the talc and the magnesium stearate are then admixed and the mixture is compressed into tablets with a breaking notch each weighing 126 mg.

EXAMPLE 54

Capsules each containing 10 mg of active ingredient, for example N-methoxycarbonylmethyl-staurosporine, are manufactured in customary manner as follows:

| Composition: |  |
| --- | --- |
| active ingredient | 2500 mg |
| talc | 200 mg |
| colloidal silica | 50 mg |

Manufacture

The active substance is intimately mixed with the talc and the colloidal silica, and the mixture is passed through a sieve having a mesh width of 0.5 mm and introduced in portions each of 11 mg into hard gelatin capsules of suitable size.

EXAMPLE 55

It is also possible to produce pharmaceutical preparations containing as active ingredient another of the compounds described in Examples 1 to 51 instead of the compound described in Examples 52 to 54.

We claim:

1. A N-substituted staurosporine compound of formula (I)

[Stau]—N(CH$_3$)—R in which

[Stau] represents a residue of the formula

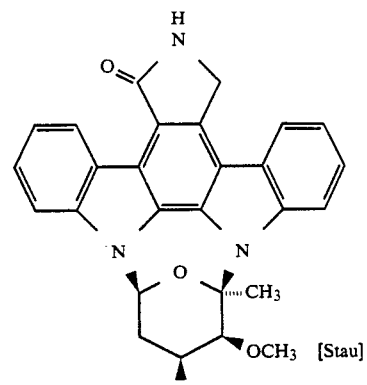

and R represents an acyl radical selected from the group consisting of:

(a) an acyl radical of the formula Z—C(=W)— in which W is oxygen or sulfur, and Z represents $C_1$-$C_7$-alkyl, which is optionally substituted by halogen, by carboxy or by $C_1$-$C_4$-alkoxycarbonyl, or phenyl, pyridyl, furyl, thienyl, imidazolyl, quinolyl, isoquinolyl, benzofuranyl or benzimidazolyl, each of which is unsubstituted or substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy, cyano or combinations thereof;

(b) an acyl radical of the formula $R_b^o$—CO— in which $R_b^o$ represents hydrogen, a $C_1$-$C_{19}$-alkyl group or such an alkyl group substituted by amino, halogen and/or carboxy in the form of a free acid, a salt, a cyano group or a $C_1$-$C_4$-alkyl ester;

(c) an acyl radical of the formula $R^o$—SO$_2$— in which $R^o$ represents $C_1$-$C_7$-alkyl or phenyl, pyridyl, furyl, thienyl, imidazolyl, quinolyl, isoquinolyl, benzofuranyl or benzimidazolyl, each of which is unsubstituted or is substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy, cyano or combinations thereof;

(d) an acyl radical of the formula $R^o$—O—CO in which $R^o$ represents $C_1$-$C_7$-alkyl or phenyl, pyridyl, furyl, thienyl, imidazolyl, quinolyl, isoquinolyl, benzofuranyl or benzimidazolyl, each of which is unsubstituted or is substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy, cyano or combinations thereof;

(e) an acyl radical of the formula

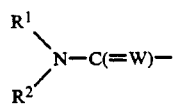

in which W represents sulfur or oxygen, $R_1$ is hydrogen and $R_2$ represents $C_1$-$C_7$-alkyl, $C_3$-$C_7$-alkenyl or phenyl, pyridyl, furyl, thienyl, imidazolyl, quinolyl, isoquinolyl, benzofuranyl or benzimidazolyl, each of which is unsubstituted or is substituted by $C_1$-$C_4$-alkyl, $C_1$-$C_4$-alkoxy, halogen, nitro, trifluoromethyl, carboxy, $C_1$-$C_4$-alkoxycarbonyl, methylenedioxy, cyano or combinations thereof;

(f) an acyl radical of a naturally occurring α-amino acid of the L series;

(g) an acyl radical of a naturally occurring α-amino acid of the L-series wherein the α-amino group is protected by an amino-protecting group, and when said α-amino acid contains a hydroxy radical, said hydroxy radical is either unprotected or protected by a hydroxy-protecting group and when said α-amino acid contains a carboxy group, said carboxy group is either unprotected or esterified by a lower alkanol or a phenyl-lower alkanol; and (h) an acyl radical of a naturally occuring α-amino acid of the L-series which carries a hydroxy radical that is protected by a hydroxy-protecting group and pharmaceutically acceptable salts thereof.

2. A compound according to claim 1 in which R represents an acyl radical of the formula Z—C(=W)— in which W is oxygen and Z represents $C_1$-$C_7$-alkyl, which is optionally substituted by halogen, by carboxy or by $C_1$-$C_4$-alkoxycarbonyl, or represents phenyl, which is unsubstituted or substituted by $C_1$-$C_4$-alkyl, $C_1$-$C_4$-alkoxy, halogen, nitro, trifluoromethyl, carboxy, or $C_1$-$C_4$-alkoxycarbonyl.

3. A N-substituted staurosporine compound of formula (I)

[Stau]—N(CH₃)—R in which [Stau] represents a residue of the formula

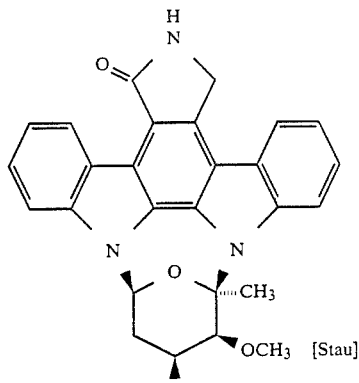

and R is derived from an α-amino acid selected from glycine, phenylglycine, alanine, phenylalanine, proline, leucine, isoleucine, tyrosine, valine, arginine, histidine, glutamic acid, aspartic acid and asparagine.

4. N-(N-tert.-butoxycarbonylaminoacetyl)-staurosporine.

5. A compound according to claim 1 selected from the group consisting of N-trifluoracetyl-staurosporine, and N-phenylcarbamoyl-staurosporine.

6. A pharmaceutical composition containing as active ingredient a pharmaceutically effective proteinkinase C inhibiting amount of at least one of the compounds defined in claim 1 together with a pharmaceutically acceptable carrier.

7. N-(3-carboxypropionyl)-staurosporine according to claim 1.

8. N-benzoyl-staurosporine according to claim 1.

9. N-methylaminothiocarbonyl-staurosporine according to claim 1.

10. A compound according to claim 1 selected from the group consisting of

N-(3-Nitrobenzoyl)-staurosporine,
N-(3-Fluorobenzoyl)-staurosporine,
N-tert.-Butoxycarbonyl-staurosporine,
N-(4-Carboxybenzoyl-staurosporine sodium salt,
N-(3,5-Dinitrobenzoyl)-staurosporine, and
N-(2-Aminoacetyl)-staurosporine.

* * * * *